US010159671B2

(12) United States Patent
Zeidan et al.

(10) Patent No.: US 10,159,671 B2
(45) Date of Patent: Dec. 25, 2018

(54) COMPOSITIONS OF MULTIPLE ARIPIPRAZOLE PRODRUGS

(71) Applicant: ALKERMES PHARMA IRELAND LIMITED, Dublin (IE)

(72) Inventors: Tarek A. Zeidan, Lexington, MA (US); David Manser, Keenagh (IE); Kristopher Perkin, Athlone (IE); Philip Cresswell, Carlow (IE); Magali Hickey, Westwood, MA (US); Brian Steinberg, Arlington, MA (US)

(73) Assignee: ALKERMES PHARMA IRELAND LIMITED, Dublin (IE)

( * ) Notice: Subject to any disclaimer, the term of this patent is extended or adjusted under 35 U.S.C. 154(b) by 0 days.

(21) Appl. No.: 15/435,170

(22) Filed: Feb. 16, 2017

(65) Prior Publication Data

US 2017/0231981 A1 Aug. 17, 2017

Related U.S. Application Data

(60) Provisional application No. 62/296,382, filed on Feb. 17, 2016.

(30) Foreign Application Priority Data

Feb. 18, 2016 (EP) .................................... 16156356

(51) Int. Cl.
*A61K 9/14* (2006.01)
*A61K 31/496* (2006.01)
(Continued)

(52) U.S. Cl.
CPC .......... *A61K 31/496* (2013.01); *A61K 9/0019* (2013.01); *A61K 9/10* (2013.01);
(Continued)

(58) Field of Classification Search
CPC ................................ A61K 9/14; A61K 31/496
See application file for complete search history.

(56) References Cited

U.S. PATENT DOCUMENTS 5,145,684 A 9/1992 Liversidge et al.
5,470,583 A 11/1995 Na et al.
(Continued)

FOREIGN PATENT DOCUMENTS

CN 015 012 236 A * 11/2015 ............... A61K 9/14
CN 105012236 A 11/2015
(Continued)

OTHER PUBLICATIONS

Turncliff et al., "Relative bioavailability and safety of aripiprazole lauroxil, a novel once-monthly, long-acting injectable atypical antipsychotic, following deltoid and gluteal administration in adult subjects with schizophrenia," *Schizophrenia Research*, vol. 159, No. 2-3, pp. 404-410 (2014).
(Continued)

*Primary Examiner* — Carlos A Azpuru
(74) *Attorney, Agent, or Firm* — Foley & Lardner LLP

(57) ABSTRACT

Described herein is a composition comprising: (a) a first population of particles of a first aripiprazole prodrug; and (b) a second population of particles of a second aripiprazole prodrug, different to the first aripiprazole prodrug. At least one of the first and second prodrug populations has a volume based particle size (Dv50) of less than about 1000 nm. Also described herein are methods of treatment using the aforementioned composition, and methods of making the aforementioned composition.

37 Claims, 6 Drawing Sheets

(51) Int. Cl.
*A61K 9/00* (2006.01)
*A61K 47/10* (2017.01)
*A61K 47/26* (2006.01)
*A61K 9/10* (2006.01)

(52) U.S. Cl.
CPC ............ *A61K 9/14* (2013.01); *A61K 9/145* (2013.01); *A61K 9/146* (2013.01); *A61K 47/10* (2013.01); *A61K 47/26* (2013.01)

(56) References Cited

U.S. PATENT DOCUMENTS

| | | |
|---|---|---|
| 5,510,118 A | 4/1996 | Bosch et al. |
| 5,518,187 A | 5/1996 | Bruno et al. |
| 5,534,270 A | 7/1996 | De Castro |
| 5,543,133 A | 8/1996 | Swanson et al. |
| 5,560,932 A | 10/1996 | Bagchi et al. |
| 5,662,883 A | 9/1997 | Bagchi et al. |
| 5,665,331 A | 9/1997 | Bagchi et al. |
| 5,718,388 A | 2/1998 | Czekai et al. |
| 5,862,999 A | 1/1999 | Czekai et al. |
| 8,431,576 B2 | 4/2013 | Remenar et al. |
| 2016/0045495 A1* | 2/2016 | Cresswell ............ A61K 31/496 424/489 |

FOREIGN PATENT DOCUMENTS

| | | |
|---|---|---|
| WO | WO 2012/12915 A1 | 9/2012 |
| WO | WO 2016/026822 A1 | 2/2016 |

OTHER PUBLICATIONS

International Search Report and Written Opinion issued in related International Patent Application No. PCT/US2017/018105, dated May 8, 2017.
Gupta et al., Nanoparticle Technology for Drug Delivery, pp. 121-131 (2006).
Aulton, "Pharmaceutical Technology, The Science of Dosage Form Design", *Pharmaceutics*, pp. 569-580 (1988).
International Preliminary Report on Patentability issued in related International Patent Application No. PCT/US2017/018105, dated Aug. 30, 2018.

* cited by examiner

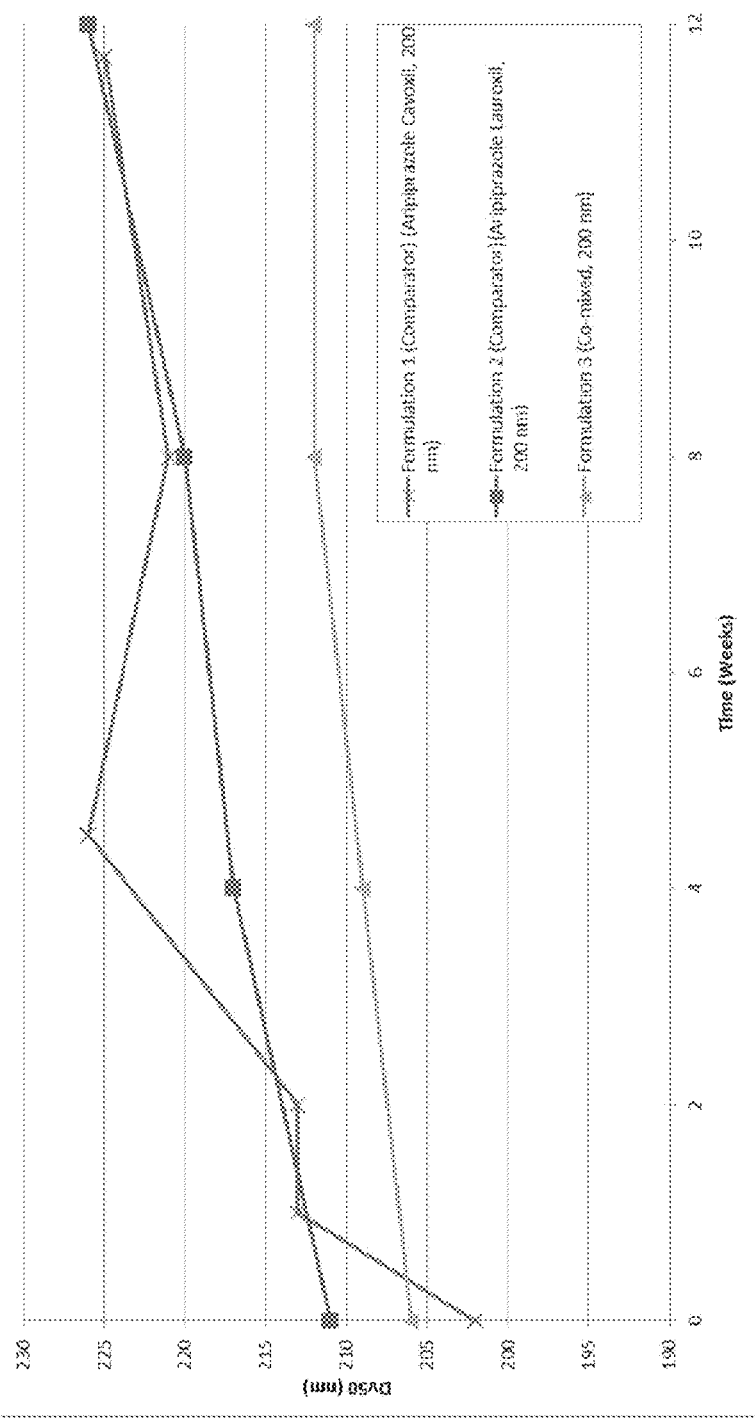

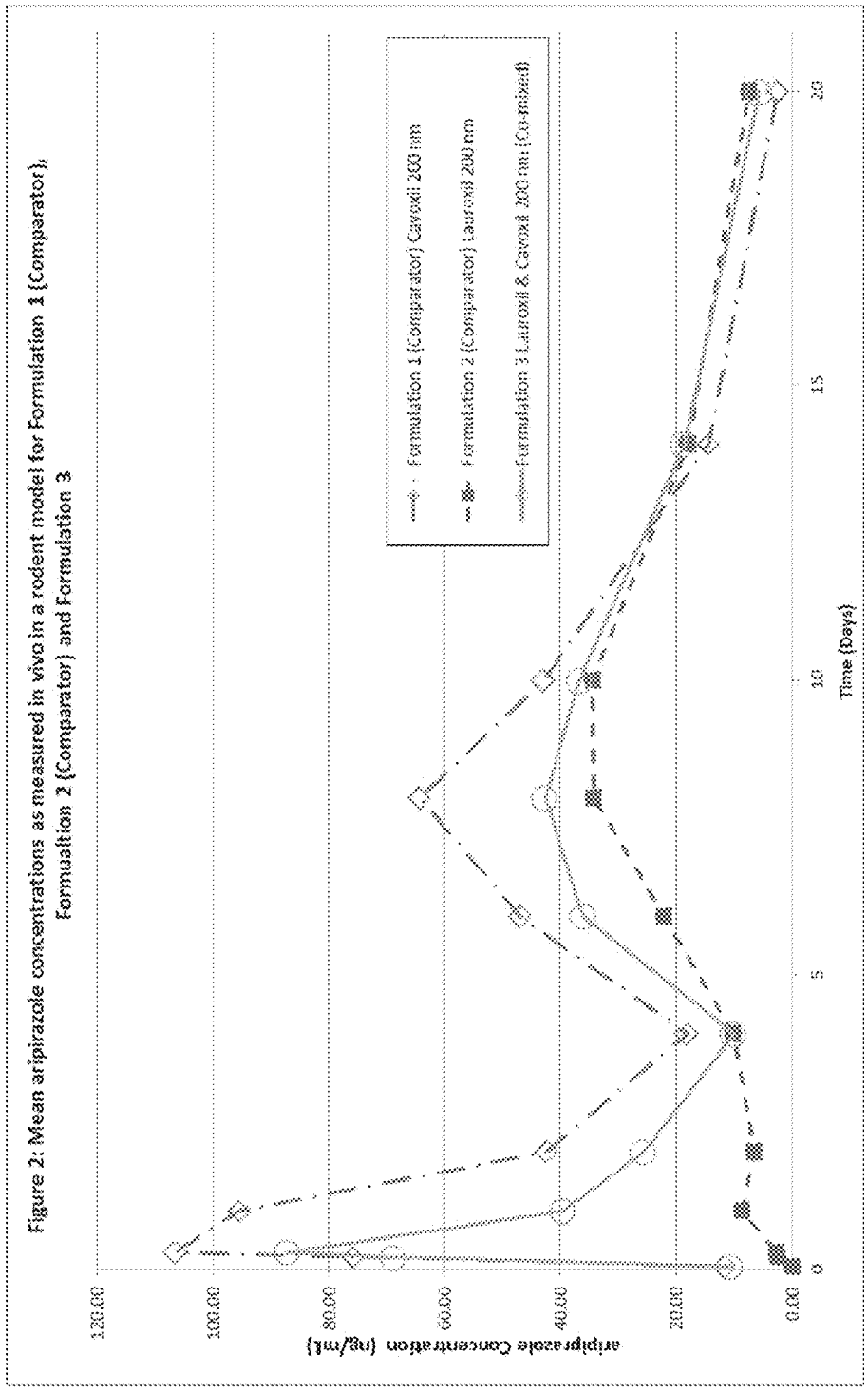

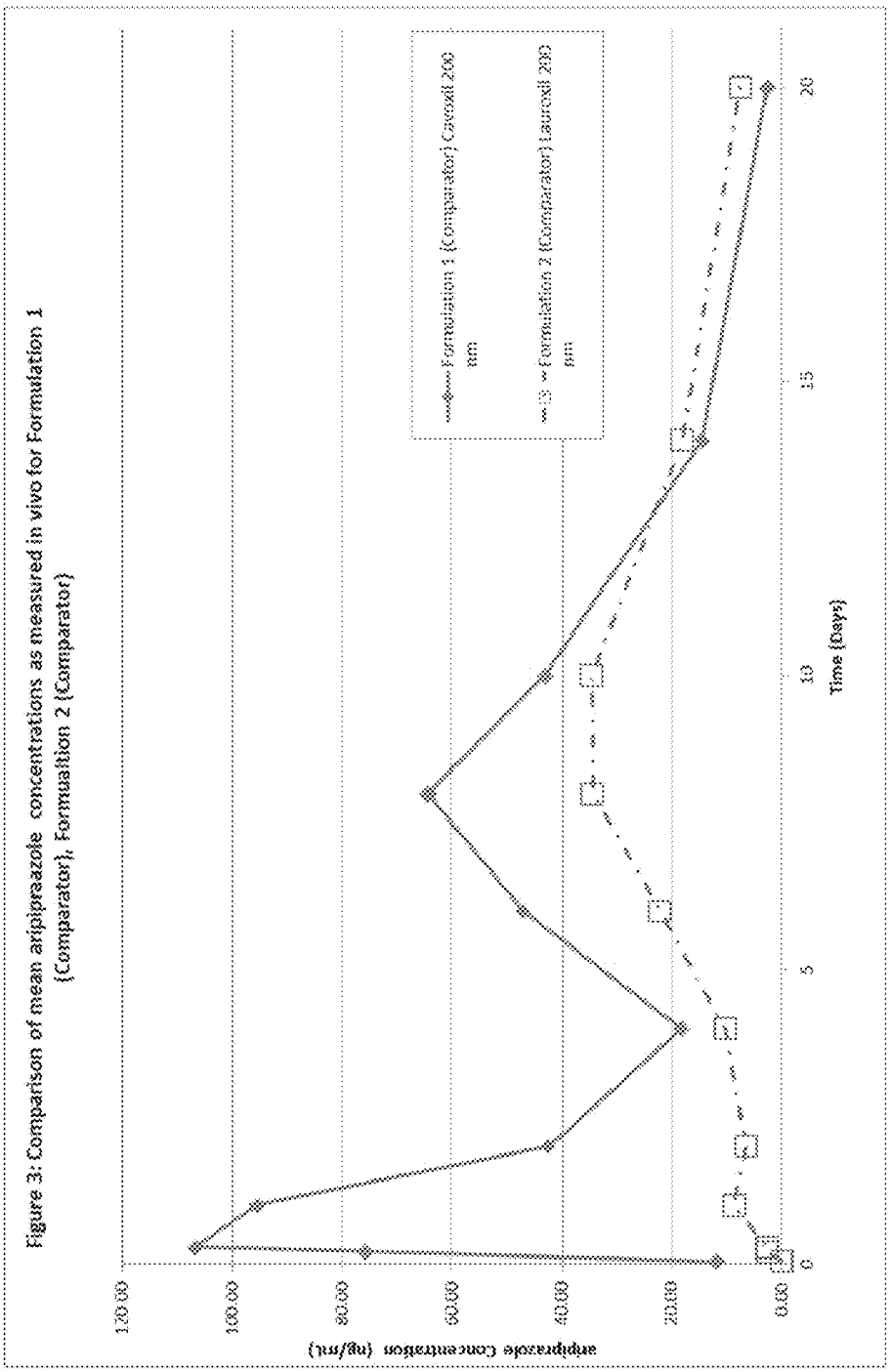

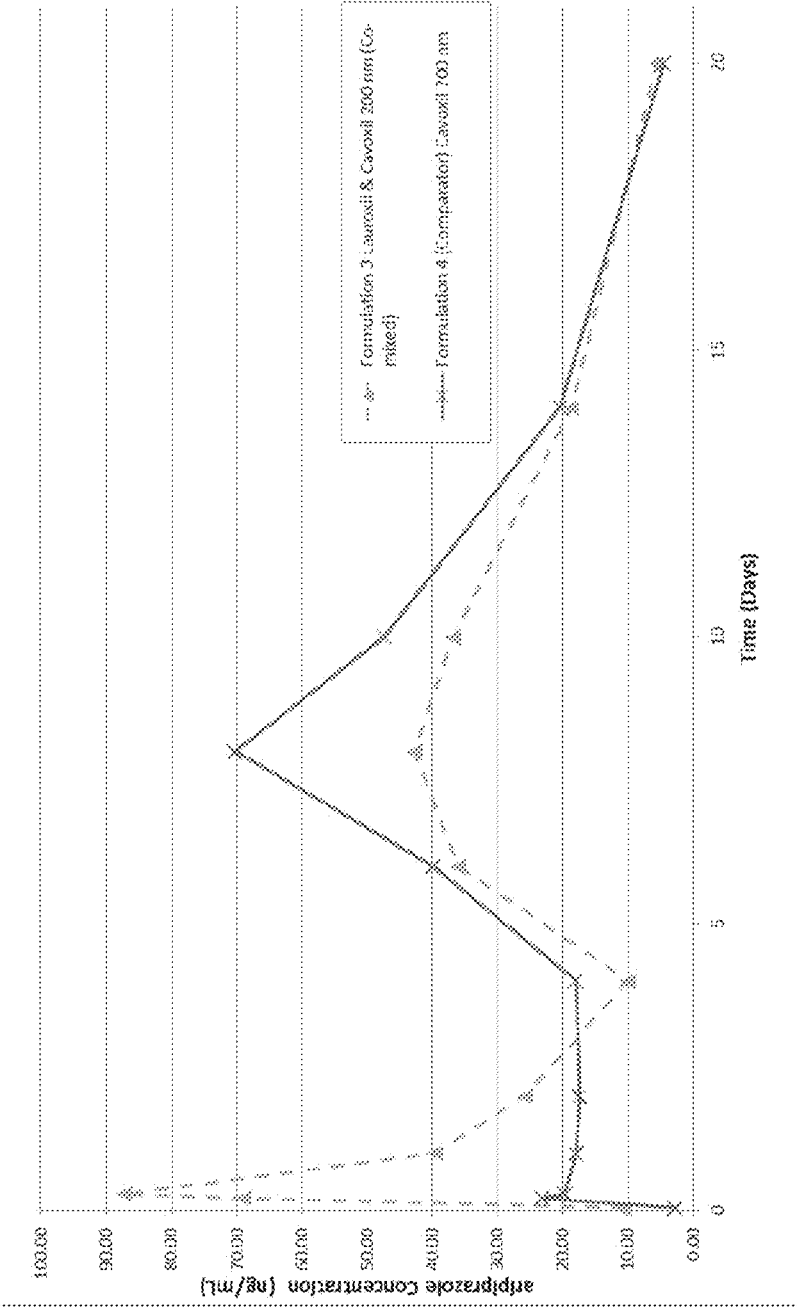

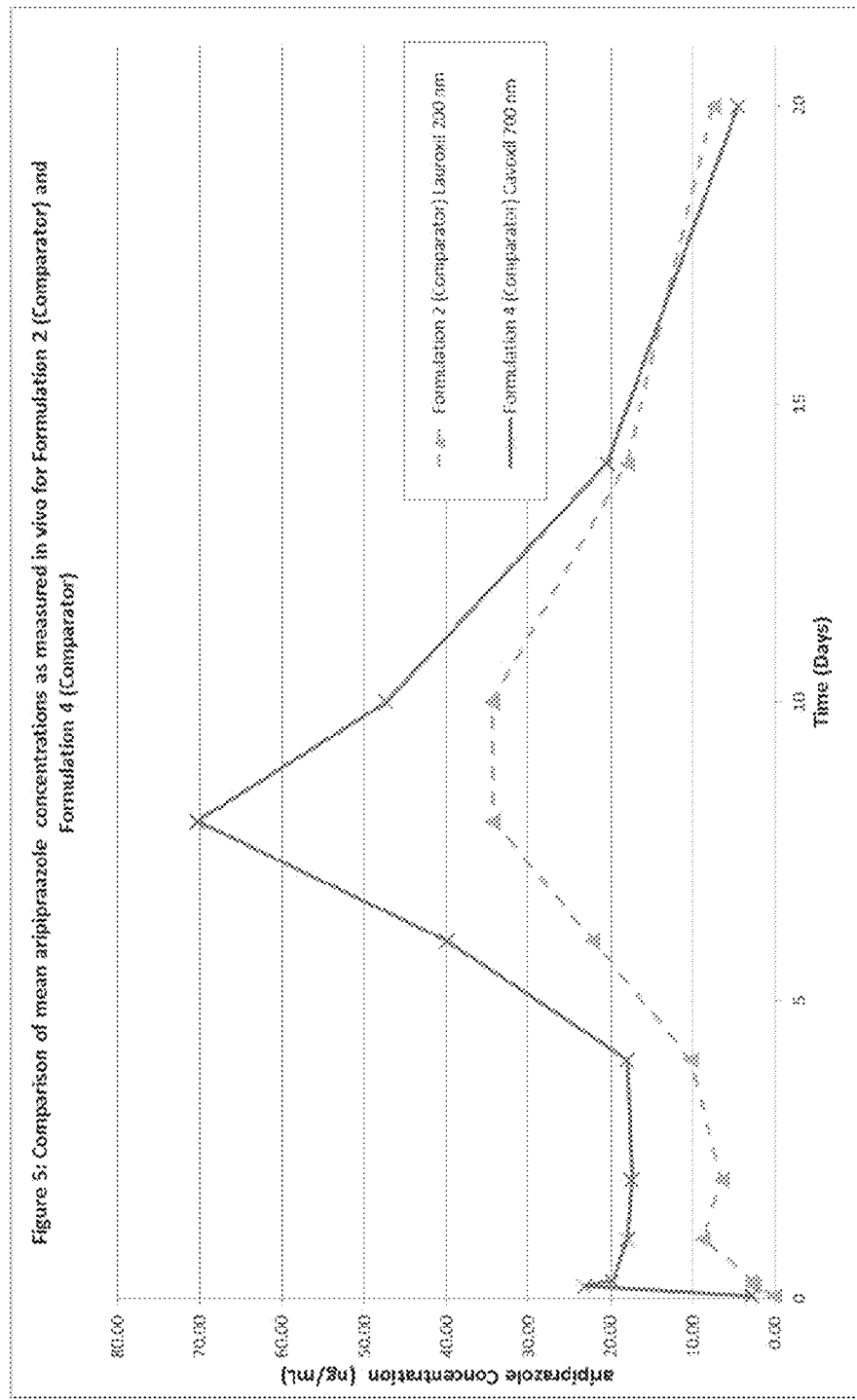

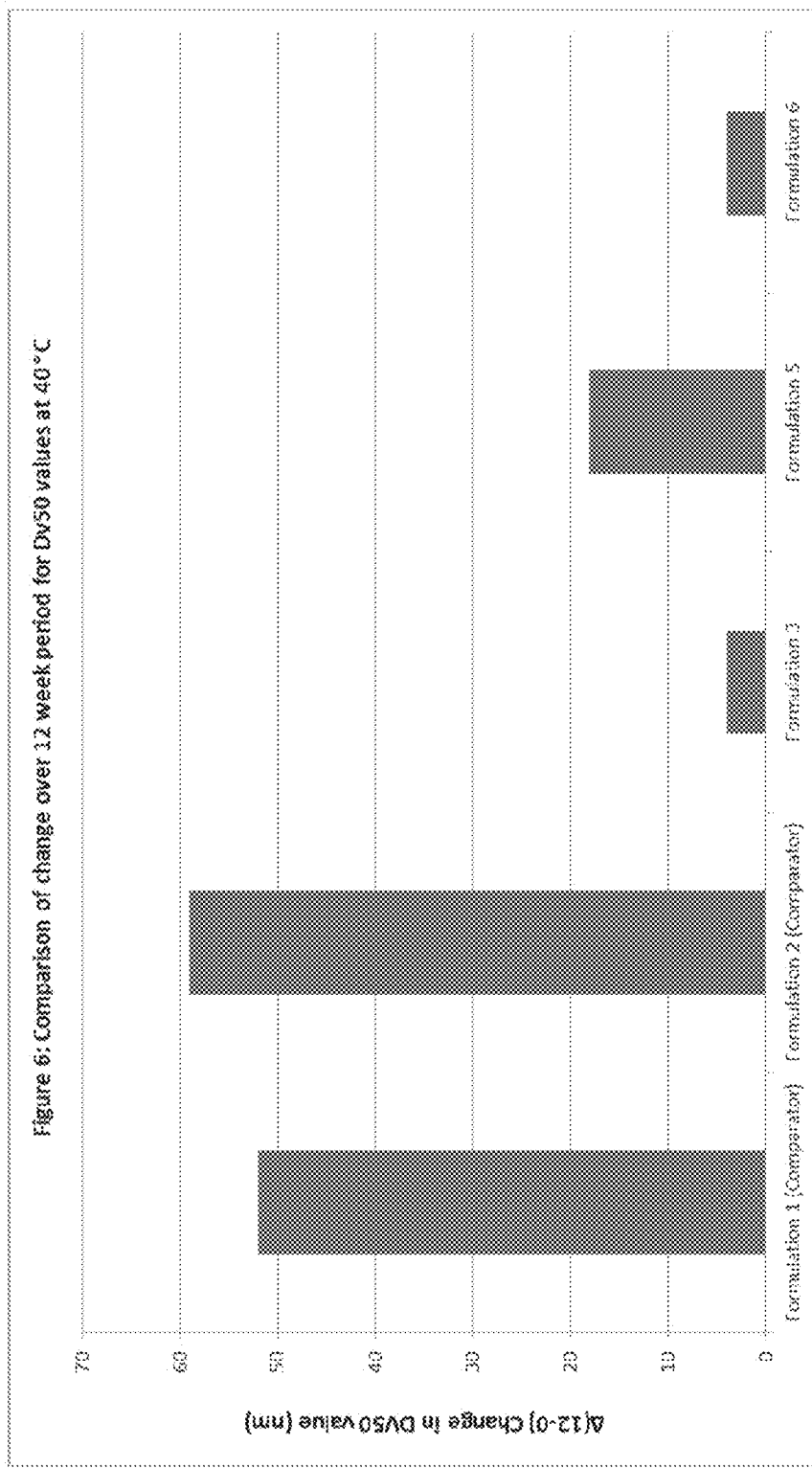

COMPOSITIONS OF MULTIPLE ARIPIPRAZOLE PRODRUGS

CROSS-REFERENCE TO RELATED APPLICATIONS

This application claims the benefit of U.S. Provisional Patent Application No. 62/296,382, filed Feb. 17, 2016, and European Patent Application No. 16156356.4, filed Feb. 18, 2016, the contents of which are incorporated herein by reference in their entirety.

FIELD OF INVENTION

The present invention is directed to compositions of aripiprazole prodrugs and their use in the treatment of various conditions.

BACKGROUND

ABILIFY MAINTENA® (aripiprazole) extended-release injectable suspension, for intramuscular use, does not reach steady state plasma concentrations in humans immediately upon its administration. Initiation therapy of Abilify Maintena® requires 14 consecutive days of concurrent oral aripiprazole (10 mg to 20 mg) with the first depot dose to achieve therapeutic concentrations (Otsuka America Pharmaceutical, Inc., "Abilify Maintena Product Insert, 2013"). Patient compliance during this 14 day lead in period presents a challenge which the present invention addresses.

SUMMARY OF THE INVENTION

The present invention is directed to composition comprising (a) a first population of particles of a first aripiprazole prodrug and (b) a second population of particles of a second aripiprazole prodrug, different to the first aripiprazole prodrug. At least one of the first and/or second populations has a volume based particle size (Dv50) of less than 1000 nm. Both aripiprazole prodrug populations have at least one surface stabilizer (a single surface stabilizer or a plurality of surface stabilizers) adsorbed on the surface of the respective aripiprazole prodrug particles. As discussed herein, it has been surprisingly discovered that such a composition comprising multiple aripiprazole prodrugs can be size stable, experiencing very little particle size growth. Furthermore, by appropriate selection of the particle size for each prodrug population. The release profile of aripiprazole in the plasma of a subject to which the composition is administered may be tailored according to any specific dosing requirements. This may be further adjusted by appropriate selection of the ratio of the weights of the respective prodrugs in the composition.

More specifically, the present invention provides a composition comprising: (a) a first population of particles of a first aripiprazole prodrug, the first population having at least one surface stabilizer adsorbed on the surface of the first aripiprazole prodrug particles, (b) a second population of particles of a second aripiprazole prodrug, the second population having at least one surface stabilizer adsorbed on the surface of the aripiprazole prodrug particles, wherein the first and second aripiprazole prodrug each have the formula below, herein referred to as Formula 1:

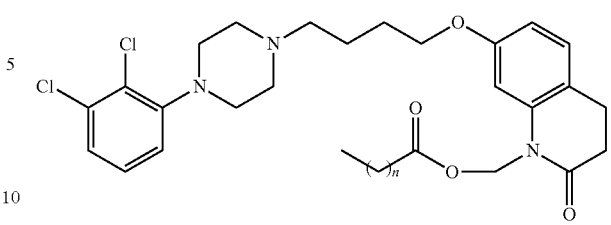

Formula 1

The value of n in the above formula is zero or an integer from 1 to 20. In compositions of the present invention, the first aripiprazole prodrug has a different value for n to that of the second aripiprazole prodrug. Furthermore, at least one of the first and second populations of particles has a volume based particle size (Dv50) of less than 1000 nm. The "at least one surface stabilizer" adsorbed to the surface of the first population of particles and the "at least one surface stabilizer" adsorbed to the second population of particles can be the same or different for both populations of particles. In a preferred embodiment a single surface stabilizer, polysorbate 20 is used to stabilize both the first and second populations of particles.

In one embodiment, in the first or second aripiprazole prodrug formula, n is equal to 4 (aripiprazole cavoxil). In another embodiment, in the first or second aripiprazole prodrug formula, n is equal to 10 (aripiprazole lauroxil). In a preferred embodiment, in the first aripiprazole prodrug formula n is equal to 4 and in the second aripiprazole prodrug formula n is equal to 10, i.e. the first aripiprazole prodrug is aripiprazole cavoxil and the second aripiprazole prodrug is aripiprazole lauroxil. In another preferred embodiment, in the first aripiprazole prodrug formula n is equal to 10 and in the second aripiprazole prodrug formula n is equal to 4, i.e. the first aripiprazole prodrug is aripiprazole lauroxil and the second aripiprazole prodrug is aripiprazole cavoxil.

Preferably the volume based particle distribution size (Dv50) of the first and/or the second population of aripiprazole prodrug particles is between 50 and 700 nm. More preferably, the volume based particle size (Dv50) of the first aripiprazole prodrug is between 100 and 300 nm and the volume based particle size of the second aripiprazole prodrug population is between 200 and 700 nm. It is believed that a composition having these particle size parameters when administered to a human or other mammalian subject would have a desirable release profile, preferably increasing the concentration of aripiprazole in the subject's blood significantly (most preferably above a therapeutically effective level) within a period of less than 48 hours and maintaining a high concentration (most preferably above a therapeutically effective level) for a period of at least about one week.

In one embodiment, the volume based particle distribution size (Dv50) of each of the first and the second populations of aripiprazole prodrug particles is between 50 and 700 nm.

In another embodiment, the volume based particle distribution size (Dv50) of the first population of aripiprazole prodrug particles is between 175 nm and 350 nm.

In another embodiment, the volume based particle size (Dv50) of the first aripiprazole prodrug is between 100 and 300 nm and the volume based particle size of the second aripiprazole prodrug population is between 200 and 700 nm.

Apart from the aforementioned embodiments, and generally speaking with respect to the compositions of the present invention, the volume based particle size (Dv50) of the first and/or second prodrug population may be less than about 1000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, or less than about 50 nm. In a preferred embodiment, the volume based particle size (Dv50) of the aripiprazole prodrug particles is between about 50 nm and 700 nm, more preferably between about 175 nm and about 350 nm.

In the compositions of the present invention, the first and second population of particles may be provided in an amount relative to each other such that the ratio of the weight of the first prodrug to the weight of the second prodrug is between 1:99 and 99:1, between 1:3 and 3:1, or more preferably between 1:1 and 1:4. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:2.1, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.25:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 99:1. Preferably, the first prodrug to which the range of ratios outlined above relates is aripiprazole cavoxil and the second prodrug is aripiprazole lauroxil.

By way of example, a composition according to the present invention may comprise at least one population of particles which is less than about 900 nm, wherein the first and second population of particles may be provided in an amount relative to each other such that the ratio of the weight of the first prodrug to the weight of the second prodrug is between 1:99 to 99:1, from 1:50 to 50:1, from 1:20 to 20:1, from 1:10, to 10:1, from 1:5 to 5:1, from 1:4 to 4:1, from 3.75:1 to 1:3.75, from 3.5:1 to 1:3.5, from 3.25:1 to 1:3.25, from 3:1 to 1:3, from 2.75:1 to 1:2.75, from 2.5:1 to 1:2.5, from 2.25:1 to 1:2.25, from 2:1 to 1:2, from 1.75:1 to 1:1.75, from 1.5:1 to 1:1.5, from 1.25:1 to 1:1.25. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:2.1, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.25:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1.13:1, 14:1, 15:1, 16:1, 17:1, 18:1, 19:1, 20:1, 30:1, 40:1, 50:1.60:1, 70:1, 80:1, 90:1, or 99:1. Preferably, in this composition, the first prodrug to which the range of ratios outlined above relates is aripiprazole cavoxil and the second prodrug is aripiprazole lauroxil.

By way of example, a composition according to the present invention may comprise at least one population of particles which is less than about 800 nm, wherein the first and second population of particles may be provided in an amount relative to each other such that the ratio of the weight of the first prodrug to the weight of the second prodrug is between 1:99 to 99:1, from 1:50 to 50:1, from 1:20 to 20:1, from 1:10, to 10:1, from 1:5 to 5:1, from 1:4 to 4:1, from 3.75:1 to 1:3.75, from 3.5:1 to 1:3.5, from 3.25:1 to 1:3.25, from 3:1 to 1:3, from 2.75:1 to 1:2.75, from 2.5:1 to 1:2.5, from 2.25:1 to 1:2.25, from 2:1 to 1:2, from 1.75:1 to 1:1.75, from 1.5:1 to 1:1.5, from 1.25:1 to 1:1.25. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:2.1, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.25:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 99:1. Preferably, in this composition, the first prodrug to which the range of ratios outlined above relates is aripiprazole cavoxil and the second prodrug is aripiprazole lauroxil.

By way of example, a composition according to the present invention may comprise at least one population of particles which is less than about 700 nm, wherein the first and second population of particles may be provided in an amount relative to each other such that the ratio of the weight of the first prodrug to the weight of the second prodrug is between 1:99 to 99:1, from 1:50 to 50:1, from 1:20 to 20:1, from 1:10, to 10:1, from 1:5 to 5:1, from 1:4 to 4:1, from 3.75:1 to 1:3.75, from 3.5:1 to 1:3.5, from 3.25:1 to 1:3.25, from 3:1 to 1:3, from 2.75:1 to 1:2.75, from 2.5:1 to 1:2.5, from 2.25:1 to 1:2.25, from 2:1 to 1:2, from 1.75:1 to 1:1.75, from 1.5:1 to 1:1.5, from 1.25:1 to 1:1.25. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:21, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.25:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 99:1. Preferably, in this composition, the first prodrug to which the range of ratios outlined above relates is aripiprazole cavoxil and the second prodrug is aripiprazole lauroxil.

By way of example, a composition according to the present invention may comprise at least one population of particles which is less than about 600 nm, wherein the first and second population of particles may be provided in an amount relative to each other such that the ratio of the weight of the first prodrug to the weight of the second prodrug is between 1:99 to 99:1, from 1:50 to 50:1, from 1:20 to 20:1, from 1:10, to 10:1, from 1:5 to 5:1, from 1:4 to 4:1, from 3.75:1 to 1:3.75, from 3.5:1 to 1:3.5, from 3.25:1 to 1:3.25, from 3:1 to 1:3, from 2.75:1 to 1:2.75, from 2.5:1 to 1:2.5, from 2.25:1 to 1:2.25, from 2:1 to 1:2, from 1.75:1 to 1:1.75, from 1.5:1 to 1:1.5, from 1.25:1 to 1:1.25. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:2.1, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.25:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 99:1. Preferably, in this composition, the first prodrug to which the range of ratios outlined above relates is aripiprazole cavoxil and the second prodrug is aripiprazole lauroxil.

By way of example, a composition according to the present invention may comprise at least one population of particles which is less than about 500 nm, wherein the first and second population of particles may be provided in an amount relative to each other such that the ratio of the weight of the first prodrug to the weight of the second prodrug is between 1:99 to 99:1, from 1:50 to 50:1, from 1:20 to 20:1, from 1:10, to 10:1, from 1:5 to 5:1, from 1:4 to 4:1, from 3.75:1 to 1:3.75, from 3.5:1 to 1:3.5, from 3.25:1 to 1:3.25, from 3:1 to 1:3, from 2.75:1 to 1:2.75, from 2.5:1 to 1:2.5, from 2.25:1 to 1:2.25, from 2:1 to 1:2, from 1.75:1 to 1:1.75, from 1.5:1 to 1:1.5, from 1.25:1 to 1:1.25. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:2.1, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.25:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1.13:1, 14:1, 15:1, 16:1, 17:1, 18:1, 19:1, 20:1, 30:1, 40:1, 50:1.60:1, 70:1, 80:1, 90:1, or 99:1. Preferably, in this composition, the first prodrug to which the range of ratios outlined above relates is aripiprazole cavoxil and the second prodrug is aripiprazole lauroxil.

By way of example, a composition according to the present invention may comprise at least one population of particles which is less than about 400 nm, wherein the first and second population of particles may be provided in an amount relative to each other such that the ratio of the weight of the first prodrug to the weight of the second prodrug is between 1:99 to 99:1, from 1:50 to 50:1, from 1:20 to 20:1, from 1:10, to 10:1, from 1:5 to 5:1, from 1:4 to 4:1, from 3.75:1 to 1:3.75, from 3.5:1 to 1:3.5, from 3.25:1 to 1:3.25, from 3:1 to 1:3, from 2.75:1 to 1:2.75, from 2.5:1 to 1:2.5, from 2.25:1 to 1:2.25, from 2:1 to 1:2, from 1.75:1 to 1:1.75, from 1.5:1 to 1:1.5, from 1.25:1 to 1:1.25. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:2.1, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.25:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 99:1. Preferably, in this composition, the first prodrug to which the range of ratios outlined above relates is aripiprazole cavoxil and the second prodrug is aripiprazole lauroxil.

By way of example, a composition according to the present invention may comprise at least one population of particles which is less than about 300 nm, wherein the first and second population of particles may be provided in an amount relative to each other such that the ratio of the weight of the first prodrug to the weight of the second prodrug is between 1:99 to 99:1, from 1:50 to 50:1, from 1:20 to 20:1, from 1:10, to 10:1, from 1:5 to 5:1, from 1:4 to 4:1, from 3.75:1 to 1:3.75, from 3.5:1 to 1:3.5, from 3.25:1 to 1:3.25, from 3:1 to 1:3, from 2.75:1 to 1:2.75, from 2.5:1 to 1:2.5, from 2.25:1 to 1:2.25, from 2:1 to 1:2, from 1.75:1 to 1:1.75, from 1.5:1 to 1:1.5, from 1.25:1 to 1:1.25. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:2.1, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.25:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 99:1. Preferably, in this composition, the first prodrug to which the range of ratios outlined above relates is aripiprazole cavoxil and the second prodrug is aripiprazole lauroxil.

By way of example, a composition according to the present invention may comprise at least one population of particles which is less than about 200 nm, wherein the first and second population of particles may be provided in an amount relative to each other such that the ratio of the weight of the first prodrug to the weight of the second prodrug is between 1:99 to 99:1, from 1:50 to 50:1, from 1:20 to 20:1, from 1:10, to 10:1, from 1:5 to 5:1, from 1:4 to 4:1, from 3.75:1 to 1:3.75, from 3.5:1 to 1:3.5, from 3.25:1 to 1:3.25, from 3:1 to 1:3, from 2.75:1 to 1:2.75, from 2.5:1 to 1:2.5, from 2.25:1 to 1:2.25, from 2:1 to 1:2, from 1.75:1 to 1:1.75, from 1.5:1 to 1:1.5, from 1.25:1 to 1:1.25. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:2.1, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.25:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 99:1. Preferably, in this composition, the first prodrug to which the range of ratios outlined above relates is aripiprazole cavoxil and the second prodrug is aripiprazole lauroxil.

By way of example, a composition according to the present invention may comprise at least one population of particles which is less than about 100 nm, wherein the first and second population of particles may be provided in an amount relative to each other such that the ratio of the weight of the first prodrug to the weight of the second prodrug is between 1:99 to 99:1, from 1:50 to 50:1, from 1:20 to 20:1, from 1:10, to 10:1, from 1:5 to 5:1, from 1:4 to 4:1, from 3.75:1 to 1:3.75, from 3.5:1 to 1:3.5, from 3.25:1 to 1:3.25, from 3:1 to 1:3, from 2.75:1 to 1:2.75, from 2.5:1 to 1:2.5, from 2.25:1 to 1:2.25, from 2:1 to 1:2, from 1.75:1 to 1:1.75, from 1.5:1 to 1:1.5, from 1.25:1 to 1:1.25. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:2.1, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.25:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1.13:1, 14:1, 15:1, 16:1, 17:1, 18:1, 19:1, 20:1, 30:1, 40:1, 50:1.60:1, 70:1, 80:1, 90:1, or 99:1. Preferably, in this composition, the first prodrug to which the range of ratios outlined above relates is aripiprazole cavoxil and the second prodrug is aripiprazole lauroxil.

Compositions according to the present invention may include a first population of aripiprazole cavoxil particles which is between than about 100 and about 1000 nm in size and a second population of aripiprazole lauroxil particles which is between about 1000) and about 25,000 nm in size, wherein the first and second population of particles are provided in an amount relative to each other such that the ratio of the weight of the first prodrug to the weight of the second prodrug is selected from the group consisting of from 1:99 to 99:1, from 1:50 to 50:1, from 1:20 to 20:1, from 1:10, to 10:1, from 1:5 to 5:1, from 1:4 to 4:1, from 3.75:1 to 1:3.75, from 3.5:1 to 1:3.5, from 3.25:1 to 1:3.25, from 3:1 to 1:3, from 2.75:1 to 1:2.75, from 2.5:1 to 1:2.5, from 2.25:1 to 1:2.25, from 2:1 to 1:2, from 1.75:1 to 1:1.75, from 1.5:1 to 1:1.5, from 1.25:1 to 1:1.25. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:2.1, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 99:1.

In another embodiment, a composition according to the present invention may include a first population of aripiprazole cavoxil particles which is between than about 100 and about 500 nm in size and a second population of aripiprazole lauroxil particles which is between about 15,000 and about 25,000 nm in size, wherein the first and second population of particles are provided in an amount relative to each other such that the ratio of the weight of the first prodrug to the weight of the second prodrug is selected from the group consisting of from 1:99 to 99:1, from 1:50 to 50:1, from 1:20 to 20:1, from 1:10, to 10:1, from 1:5 to 5:1, from 1:4 to 4:1, from 3.75:1 to 1:3.75, from 3.5:1 to 1:3.5, from 3.25:1 to 1:3.25, from 3:1 to 1:3, from 2.75:1 to 1:2.75, from 2.5:1 to 1:2.5, from 2.25:1 to 1:2.25, from 2:1 to 1:2, from 1.75:1 to 1:1.75, from 1.5:1 to 1:1.5, from 1.25:1 to 1:1.25. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:2.1, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.25:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 99:1.

In a preferred embodiment, a composition according to the present invention includes a first population of aripiprazole cavoxil particles which is between than about 100 and about 300 nm in size and a second population of aripiprazole lauroxil particles which is between about 100 and about 700 nm in size, wherein the first and second population of particles are provided in an amount relative to each other such that the ratio of the weight of the first prodrug to the weight of the second prodrug is selected from the group consisting of from 1:99 to 99:1, from 1:50 to 50:1, from 1:20 to 20:1, from 1:10, to 10:1, from 1:5 to 5:1, from 1:4 to 4:1, from 3.75:1 to 1:3.75, from 3.5:1 to 1:3.5, from 3.25:1 to 1:3.25, from 3:1 to 1:3, from 2.75:1 to 1:2.75, from 2.5:1 to 1:2.5, from 2.25:1 to 1:2.25, from 2:1 to 1:2, from 1.75:1 to 1:1.75, from 1.5:1 to 1:1.5, from 1.25:1 to 1:1.25. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:2.1, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.25:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 99:1.

With respect to each of the aforementioned exemplary compositions, it is preferable if the surface stabilizer adsorbed to the first and second population of particles is polyoxyethylene sorbitan monolaurate (also known as polysorbate 20).

Generally speaking with respect to the compositions of the present invention the surface stabilizer or surface stabilizers adsorbed to the first and/or the second population of particles may be selected from a preferred group consisting of a polyoxyethylene sorbitan fatty acid ester (such as polysorbate 80 (polyoxyethylene sorbitan monooleate), polysorbate 40 (polyoxyethylene sorbitan monopalmitate), polysorbate 20 (polyoxyethylene sorbitan monolaurate), for example sold under the TWEEN® trade name (Croda Americas, LLC; Delaware, USA)), low molecular weight povidones, lecithin, d-alpha tocopheryl polyethylene glycol 1000 succinate, dioctyl sodium sulfosuccinate (or docusate sodium), methyl and propyl parabens, sorbitan monolaurate, carboxymethyl cellulose, hydroxypropylcellulose, sodium deoxycholate, akylsaccharides, difunctional block copolymers, d-alpha tocopheryl polyethylene glycol 1000 succinate, gelatin, albumin, lysozyme, cyclodextrins, polyoxyethylene-polyoxypropylene block copolymers, polyethylene glycols (such as PEG1000 and PEG4000) and gel forming polymers. Most preferably, the surface stabilizer is selected from the group comprising polysorbate 20 (polysorbate monolaurate), a polyoxyethylene-polyoxypropylene block copolymer (preferably having an average molecular weight of between about 7,500 and 10,000 such as that sold under the trade name Pluronic® F68 (BASF Corp; New Jersey, USA) which has an average molecular weight of 8,400) and PEG4000.

More preferably, the at least one surface stabilizer(s) is/are selected from the group consisting of polyoxyethylene sorbitan monolaurate (polysorbate 20), a polyoxvethylene-polyoxypropylene block copolymer having an average molecular weight of about 8,400 (e.g., Pluronic® F68) and the polyethylene glycol PEG4000. The aforementioned were found to be particularly useful in terms of improving the rate of release of aripiprazole from the compositions and improving the stability of the compositions over a period of time.

The ratio of the first and second prodrug to surface stabilizer in the compositions of the present invention may be within the range from about 0.1:1 to about 40:1.

One composition of the invention comprises a population of aripiprazole lauroxil particles, a population of aripiprazole cavoxil particles and at least one surface stabilizer, each of said populations of aripiprazole prodrug particles having a particle size selected from those specified above and said aripiprazole prodrugs being present in a weight ratio selected from those specified above, wherein the at least one surface stabilizer includes polysorbate monolaurate.

Another composition of the invention comprises a population of aripiprazole lauroxil particles, a population of aripiprazole cavoxil particles and at least one surface stabilizer, each of said populations of aripiprazole prodrug particles having a particle size selected from those specified above and said aripiprazole prodrugs being present in a weight ratio selected from those specified above, wherein the at least one surface stabilizer is (or includes) a polyoxyethylene-polyoxypropylene block copolymer having an average molecular weight of about 8,400, such as that sold under the trade name Pluronic® F68 (BASF Corp.; New Jersey, USA).

A further composition of the invention comprises a population of aripiprazole lauroxil particles, a population of aripiprazole cavoxil particles and at least one surface stabilizer, each of said populations of aripiprazole prodrug particles having a particle size selected from those specified above and said aripiprazole prodrugs being present in a weight ratio selected from those specified above, wherein the at least one surface stabilizer includes PEG4000.

A further composition of the invention comprises a population of aripiprazole lauroxil particles, a population of aripiprazole cavoxil particles and both polyoxvethylene sorbitan monolaurate (polysorbate 20) and a polyoxyethylene-polyoxypropylene block copolymer having an average molecular weight of about 8,400 (e.g., Pluronic® F68) as surface stabilizers. Each of said populations of aripiprazole prodrug particles has a particle size selected from those specified above and said aripiprazole prodrugs being present in a weight ratio selected from those specified above. Such a composition may exhibit a particularly fast rate of release of aripiprazole, potentially being useful where therapeutic coverage over early time points after administration is desired.

A further composition of the invention comprises a population of aripiprazole lauroxil particles, a population of aripiprazole cavoxil particles and both polyoxyethylene sorbitan monolaurate (polysorbate 20) and the polyethylene glycol PEG4000 as surface stabilizers. Each of said populations of aripiprazole prodrug particles has a particle size selected from those specified above and said aripiprazole prodrugs being present in a weight ratio selected from those specified above. Such a composition may exhibit improved particle size stability (i.e., reduced particle size growth) over time.

The composition of the present invention may further comprise a dispersion medium in which the first aripiprazole prodrug population of particles and the second aripiprazole prodrug population of particles is dispersed.

Compositions of the present invention may be adapted for administration as a depot injection. Optionally and additionally, the composition is provided in an injection device.

The injection device may be, for example, a pre-filled syringe, auto-injector, needleless syringe or dual chambered syringe.

Preferably, compositions of the present invention, when dosed in a mammalian subject, reach a therapeutically effective level within 24 hours.

Compositions of the present invention as described herein may be useful in the treatment of a condition in a mammal selected from schizophrenia, bipolar I disorder, major depressive disorder (MDD), autistic disorder, agitation associated with schizophrenia or bipolar I disorder, wherein said treatment comprises (a) the administration of a composition having a first population of particles of a first aripiprazole prodrug and a second population of particles of a second aripiprazole prodrug, wherein at least one of the populations has a volume based particle size (Dv50) of less than 1000 nm, to the mammal. The treatment may further comprise (b) the administration of a second composition of aripiprazole prodrug having a volume based particle size (Dv50) of greater than about 5000 nm to the mammal.

Compositions of the invention may be useful in the treatment of a condition in a mammal selected from schizophrenia, bipolar I disorder, major depressive disorder (MDD), autistic disorder, agitation associated with schizophrenia or bipolar I disorder. Said treatment comprises the administration of a first aripiprazole prodrug having the formula:

Formula 3

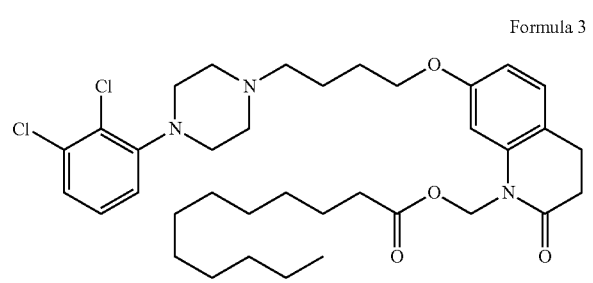 [SMILES: CCCCCCCCCCCC(=O)OCN1C(=O)CCc2ccc(OCCCCN3CCN(c4cccc(Cl)c4Cl)CC3)cc21]

and a second aripiprazole prodrug composition having the formula:

Formula 2

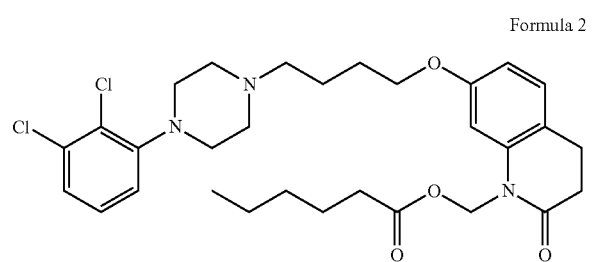 [SMILES: CCCCCC(=O)OCN1C(=O)CCc2ccc(OCCCCN3CCN(c4cccc(Cl)c4Cl)CC3)cc21]

In said embodiment, the mixture of aripiprazole prodrugs has a volume based particle distribution size (Dv50) of about 200 nm, and the ratio the first aripiprazole prodrug to the second aripiprazole prodrug is 1:3.

The present invention further includes a method of treatment of a condition in a mammal selected from schizophrenia, bipolar I disorder, major depressive disorder (MDD), autistic disorder, agitation associated with schizophrenia or bipolar I disorder. The method comprises (a) the administration of a composition having a first population of particles of a first aripiprazole prodrug and a second population of particles of a second aripiprazole prodrug, wherein at least one of the populations has a volume based particle size (Dv50) of less than about 1000 nm, to the mammal. The method may further comprise (b) the administration of a second composition of aripiprazole prodrug having a volume based particle size (Dv50) of greater than about 5000 nm to the mammal.

The present invention further includes a method for preparing the composition described herein, the method comprising the following steps which may or may not be carried out in sequential order: (a) calculating a quantity of at least one stabilizer to be added to the composition, (b) producing a first population of aripiprazole prodrug particles having a volume based particle size (Dv50) of less than about 1000 nm, as determined by light scattering, (c) producing a second population of a second aripiprazole prodrug, different to the first aripiprazole prodrug, and having a volume based particle size (Dv50) of greater, equal or less than about 1000 nm, (d) combining a quantity of at least one surface stabilizer with the first and second populations of aripiprazole prodrug particles, such that the at least one surface stabilizer is adsorbed to the surface of the particles of the first and second particle populations. Optionally, steps (b), (c) and (d) may be performed simultaneously by milling the respective first and second aripiprazole prodrugs together with the at least one stabilizer present. Alternatively, steps (b), (c) and (d) are performed separately and the method includes the further step of (e) mixing the first and second populations of particles together after steps (c) and (d) are carried out.

In a further embodiment, the present invention comprises a composition consisting of a mixture of a population of particles of a first aripiprazole prodrug and a second aripiprazole prodrug composition having the formula:

Formula 1

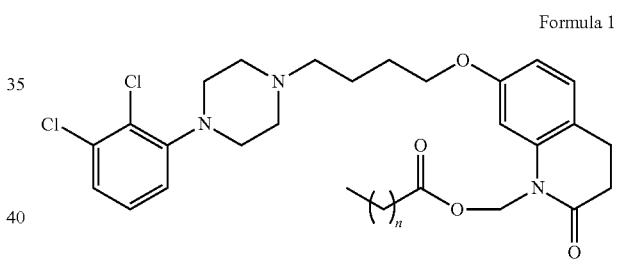

wherein n is zero or an integer less than 20, and wherein the volume based particle size (Dv50) of the first aripiprazole prodrug is between about 100 and about 300 nm and the volume based particle size of the second aripiprazole prodrug population is between about 200 and about 700 nm, and wherein the ratio the first aripiprazole prodrug to the second aripiprazole prodrug is 1:3.

The present invention is further directed to a method of adapting the initial in vivo pharmacokinetic release profile said method comprising administering to a subject a mixture of a population of particles of a first aripiprazole prodrug having the formula:

Formula 3

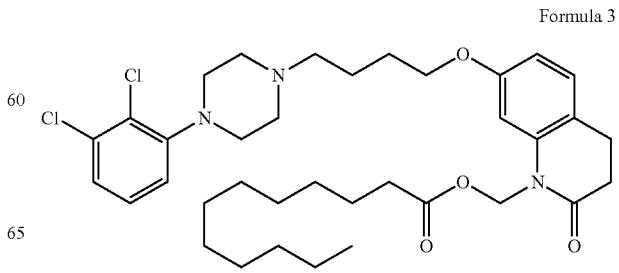

and a second aripiprazole prodrug composition having the formula:

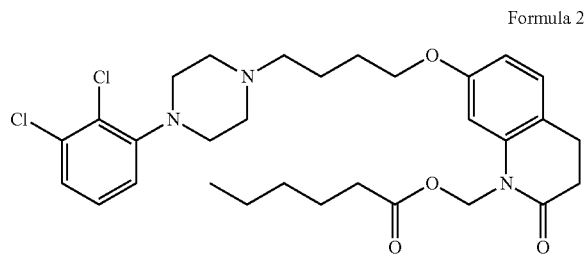 [SMILES: CCCCCC(=O)OCN1C(=O)CCc2ccc(OCCCCN3CCN(c4cccc(Cl)c4Cl)CC3)cc21]

Formula 2 wherein the mixture of aripiprazole prodrugs has a volume based particle distribution size (Dv50) of about 200 nm, wherein the ratio of the first aripiprazole prodrug to the second aripiprazole prodrug is about 1:3; such that the composition achieves a therapeutic concentration of aripiprazole in about 24 hours.

BRIEF DESCRIPTION OF THE DRAWINGS

FIG. 1 is a comparison of Dv50 values for Formulation 1 (Comparator), Formulation 2 (Comparator) and Formulation 3 observed over a period of 12 weeks during a stability study at a temperature of 25° C.

FIG. 2 is a plot of the mean aripiprazole concentrations as measured in vivo in a rodent model for Formulation 1 (Comparator), Formulation 2 (Comparator) and Formulation 3.

FIG. 3 is a comparison of the mean aripiprazole concentrations as measured in vivo for Formulation 1 (Comparator), and Formulation 2 (Comparator).

FIG. 4 is a comparison of the mean aripiprazole concentrations as measured in vivo for Formulation 3 and Formulation 4 (Comparator).

FIG. 5 is a comparison of the mean aripiprazole concentrations as measured in vivo for Formulation 2 (Comparator) and Formulation 4 (Comparator).

FIG. 6 is a comparison of Dv50 values of Formulations 1-3 and 5-6 over a 12 week period when stored at 40° C.

DETAILED DESCRIPTION

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

A "long acting injectable" or "depot" injection is an injectable composition (usually subcutaneous or intramuscular) which, upon injection, forms a reservoir of the drug substance within the body of the subject from which the drug is slowly distributed into systemic circulation. In this way the drug may be delivered in a controlled fashion over a prolonged period. As defined herein, a depot injection releases the aripiprazole prodrug over an extended period of time (e.g., at least about 24 hours and preferably about 1 week or more).

The term "lead in composition" as used herein refers to a formulation of an active agent which reduces or eliminates the "lead in" period, as referenced below. In other words, a lead in composition acts to increase the active agent levels during the lead in period over and above the level of what would be observed in the absence of the lead in composition. This may also be referred to as a loading dose.

The term "lead in" or "lead in period" as used herein refers to a period of time following administration of an active agent to a subject before the level of active agent in systemic circulation reaches a therapeutically effective amount for the mammalian subject to which it is dosed.

The term "particle size" or "volume based particle size" or "volume based particle size distribution" as used herein is equivalent to and also referred to as the Dv50 or D50 and means that at least about 50% of the aripiprazole prodrug particles have a diameter of less than the size specified. The aforementioned terms are used interchangeably herein. For example a volume based particle size (Dv50) of less than about 1000 nm, means that 50% of the particle population has a diameter of less than about 1000 nm when measured by static or dynamic light scattering techniques known to those skilled in the art. Since the particles of the present invention tend to be irregular in shape, an approximation of the particle size is made on the basis of the volume based particle size, which specifies the diameter of the sphere that has the same volume as a given particle. Unless otherwise specified, all particle sizes are specified in terms of volume based measurements and are measured by laser light scattering/diffraction. Particle sizes are then determined based on Mie scattering theory. More specifically, unless otherwise specified, volume based particle size (Dv50) is determined using a Horiba LA-950 standard model laser particle size analyser. Deionized water or water with a small quantity (for example 0.1% w/w) of surface stabilizer (for example polysorbate 20) is used as the sizing medium unless otherwise specified. The terms "D90" and "D10" mean that, respectively at least about 90% and 10% of the aripiprazole prodrug particles have a diameter of less than the size specified. These may also be referred to as "Dv90" and "Dv10" respectively, and these terms are used interchangeably herein.

The term "mean particle size" is essentially the same as "volume mean diameter" and in the present application this is defined in the same manner as defined in the Horiba Scientific brochure. "A guidebook to particle size analysis" (2012), available from Horiba's website, www.horiba.com. The calculation is expressed by conceptualizing a histogram table showing the upper and lower limits of n size channels along with the percent within each channel. The Di value for each channel is the geometric mean, the square root of the product of the upper and lower diameters. For the numerator, take the geometric Di to the fourth power times the percent in that channel, summed over all channels. For the denominator, take the geometric Di to the third power times the percent in that channel, summed over all channels. The volume mean diameter is referred to by several names including D[4,3].

$$D[4,3] = \frac{\sum_1^n D_i^4 v_i}{\sum_1^n D_i^3 v_i}$$

The skilled person will appreciate that particle size can also be determined by other suitable measurement means (such as by volume, number, etc.), and can be measured by, for example, sedimentation flow fractionation, dynamic light scattering, disk centrifugation, and other techniques known in the art. Further details of dynamic and static light scattering techniques are provided in "Nanoparticle Technology For Drug Deliver," by Ram B. Gupta and Uday B. Kompella, published by Taylor & Francis Group ISBN 1-57444-857-9 (pages 121-131) and "Pharmaceutics, The Science Of Dosage Form Design", First Edition, edited by Michael E. Aulton and published by Churchill Livingstone ISBN 0-443-03643-8 (pages 569-580).

A "prodrug" is a therapeutically inactive molecule which can be physiologically metabolized into an active pharmaceutical ingredient. The terms "drug" or "active agent," when used herein, typically refers to aripiprazole (the metabolite), but may, if clearly indicated by its context, refer to another drug.

A "size stable" composition is a composition that exhibits no flocculation or particle agglomeration visible to the naked eye for at least about 15 minutes, and preferably, at least about two days or longer after preparation. Preferably, a "size stable" composition is a composition where the volume based particle size (Dv50) and/or mean particle size does not increase by any more than about 400 nm when the composition is stored at about 25° C. for a period of about 24 hours. More preferably, a "size stable" composition has a volume based particle size (Dv50) and/or mean particle size that does not increase by any more than about 400 nm when the composition is stored at about 40° C. for a period of about 6 months. Most preferably, a "size stable" composition has a volume based particle size (Dv50) and/or mean particle size that does not increase by any more than about 200 nm when the composition is stored at about 40° C. for a period of about 6 months.

As used herein, the term "subject" is used to mean an animal, preferably a mammal, including a human or a non-human. The terms patient and subject may be used interchangeably.

The term "therapeutically effective amount" refers to the minimum blood concentration of aripiprazole required in order to have a therapeutic effect. This may vary depending on the type of subject. This value in relation to humans may be at least about 34 to about 50 ng/mL, and preferably about 94 ng/mL.

The terms "treatment," "therapy." "therapeutic" and the like, as used herein, encompass any course of medical intervention aimed at a pathologic condition, and includes not only permanent cure of a disease, but prevention of disease, control or even steps taken to mitigate a disease or disease symptoms.

Aripiprazole Prodrugs of the Present Invention

Compositions of the present invention comprise certain aripiprazole prodrugs which are described in U.S. Pat. No. 8,431,576, which is specifically incorporated by reference herein. In particular, the aripiprazole prodrug referenced in relation to the present invention has the general formula (hereinafter referred to as "Formula 1"):

Formula 1

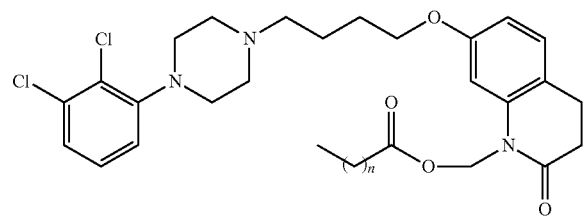

Where n is any whole number greater than or equal to 0 and less than 20. In the preferred embodiments discussed below, n is equal to 4 or 10. The value of n may also be referred to herein as the "chain length" of the aripiprazole prodrug in question.

The present invention is directed to a composition comprising at least two aripiprazole prodrugs having the same general formula as described above, but wherein one prodrug has a different chain length to the other. The term "different aripiprazole prodrug" when referring to an earlier described aripiprazole prodrug means that n is a different whole number for each respective aripiprazole prodrug. "Different aripiprazole prodrugs" means a plurality of aripiprazole prodrugs having the above formula in which n is a different whole number for each respective prodrug.

One such compound is aripiprazole hexanoate (in this case, n=4), the USAN term for which is aripiprazole cavoxil. Aripiprazole cavoxil is the N-hexanoyloxymethyl prodrug of aripiprazole and has the following structure (hereinafter referred to as "Formula 2"):

Formula 2

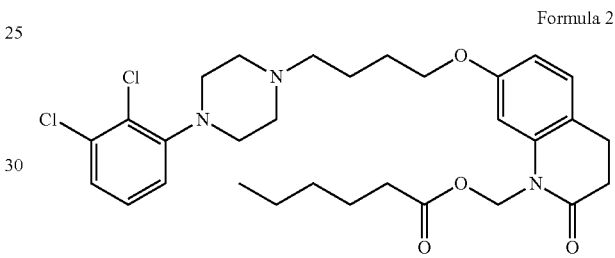

The above compound may be described by the chemical name (7-(4-(4-(2,3-Dichlorophenyl)piperazin-1-yl)butoxy)-2-oxo-3,4-dihydroquinolin-1(2H)yl)methyl hexanoate and the molecular formula $C_{30}H_{39}Cl_2N_3O_4$. The molecule has the CAS registry number 1259305-26-4.

Another such compound is aripiprazole laurate (in this case n=10). The USAN term for which is aripiprazole lauroxil. Aripiprazole lauroxil is the N-lauroyloxymethyl prodrug of aripiprazole and has the following structure (hereinafter referred to as "Formula 3"):

Formula 3

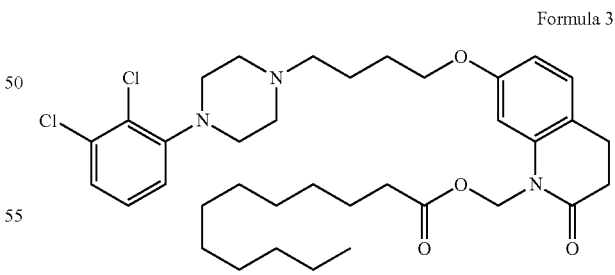

This above compound can be described by the chemical name Dodecanoic acid, [7-[4-[4-(2,3-dichlorophenyl)-1-piperazinyl]butoxy]-3,4-dihydro-2-oxo-1(2H)-quinolinyl] methyl ester and the molecular formula $C_{36}H_{51}Cl_2N_3O_4$. The molecule has the CAS registry number 1259305-29-7.

Aripiprazole lauroxil is a long acting injectable indicated for schizophrenia developed by Alkermes Pharma Ireland Limited in the form of a microcrystalline suspension having a particle size in the order of about 20 μm.

Relationship Between Release Profile, Aripiprazole Prodrug Selection and Particle Size In the compositions of the present invention, a number of factors can impact the in vivo concentration of aripiprazole in the blood of a subject over a given time period, hereinafter referred to as the "in vivo release profile of aripiprazole". As described earlier, the present invention is directed to compositions comprising two or more distinct aripiprazole prodrugs, in which the value of n, or the chain length, is different for each prodrug. Variation of the chain length of each respective prodrug results in variation of the rate of dissolution of that prodrug. In a general sense, the effective rate at which aripiprazole becomes available in the subject's blood is inversely related to the chain length of the aripiprazole prodrug, with longer chain lengths dissolving more slowly, resulting in slower appearance of the active moiety/moieties in the blood of the subject, and shorter chain lengths dissolving more quickly, resulting in a faster appearance of the active moieties in the blood of the subject. Where a shorter chain aripiprazole prodrug is administered to a subject, the prodrug will release faster to provide a concentration of aripiprazole in the blood of the subject above the therapeutically effective amount (hereinafter referred to as "therapeutic coverage") over the earlier time points of the in vivo release profile. These concentrations will then drop over a period of time as the active is being excreted and/or metabolized within the body. Conversely, for longer chain length aripiprazole prodrugs the active moieties become bioavailable at a later point in time since the rate of release is slower. Therefore, longer chain length aripiprazole prodrugs provide therapeutic coverage during later time points. The present inventors have recognized that by appropriate selection of two or more aripiprazole prodrugs of different chain lengths, it is possible to achieve therapeutic coverage in the in vivo release profile over a greater number of time points in comparison to a composition with a single aripiprazole prodrug.

The present invention recognises another factor affecting the timepoints of the in vivo release profile for which therapeutic coverage is achieved, namely the particle size when the aripiprazole prodrug is provided in particulate form. The rate of dissolution of a given aripiprazole prodrug may be increased by decreasing the particle size. For example, assuming all factors in a composition are the same, a composition of less than 1000 nm will result in a faster dissolution profile and a faster in vivo release of both the prodrug and active moiety than a similar composition having a particle size of greater than 10 microns.

The present invention is directed to compositions comprising at least two aripiprazole prodrugs of differing chain lengths, each in a particulate form wherein at least one of the particle populations has a particle size of less than about 1000 nm. The particle size for each particle population may be the same or different. Where the populations have different particle sizes, one or more populations may have a volume based particle size (Dv50) of less than about 1000 nm, in which case it is referred to herein as a "nanoparticle population," or where a population has a particle size of greater than about 1000 nm, in which case it is referred to herein as a "microparticle population." As discussed herein, appropriate selection of the aripiprazole chain length for each prodrug and the particle size of the populations allows the in vivo release profile to be tailored such as to provide a higher aripiprazole concentration: preferably above therapeutically effective levels over desired time points, providing significant flexibility in dosage form design.

Unexpectedly, when dosed in vivo, the pharmacokinetic profile obtained for compositions of the present invention in which particle populations of two distinct aripiprazole prodrugs are present, essentially combined in an additive fashion the characteristics of the pharmacokinetic profiles that are obtained when the same particulate populations are administered individually and separately. It is thereby possible to increase the overall range of timepoints over which therapeutic coverage is obtained by combining the profiles of the individual prodrug populations within the composition. There is no precedent in the art to suggest that the individual pharmacokinetic profiles combine in this fashion when two different aripiprazole prodrug populations are combined in a single composition.

Aripiprazole Prodrug Ratio as a Means to Further Tailor Release Profile

The present inventors have also recognised that the in vivo release profile of aripiprazole (concentrations of aripiprazole measured in the blood) in a subject to which a composition according to the present invention is administered may be further varied by adjusting the relative proportions of the respective prodrugs. For example, the two aripiprazole prodrugs in the compositions of the present invention may be provided in an amount relative to each other such that the ratio of the respective % (w/w) quantities of the first prodrug to the second prodrug may be within the range from 1:99 to 99:1, from 1:50 to 50:1, from 1:20 to 20:1, from 1:10, to 10:1, from 1:5 to 5:1, from 1:4 to 4:1, from 3.75:1 to 1:3.75, from 3.5:1 to 1:3.5, from 3.25:1 to 1:3.25, from 3:1 to 1:3, from 2.75:1 to 1:2.75, from 2.5:1 to 1:2.5, from 2.25:1 to 1:2.25, from 2:1 to 1:2, from 1.75:1 to 1:1.75, from 1.5:1 to 1:1.5, from 1.25:1 to 1:1.25. More specifically, the ratio may be 1:99, 1:90, 1:80, 1:70, 1:60, 1:50, 1:40, 1:30, 1:20, 1:19, 1:18, 1:17, 1:16, 1:15, 1:14, 1:13, 1:12, 1:11, 1:10, 1:9, 1:8, 1:7.5, 1:7, 1:6.5, 1:6, 1:5.75, 1:5.5, 1:5.25, 1:5, 1:4.9, 1:4.8, 1:4.75, 1:4.7, 1:4.6, 1:4.5, 1:4.4, 1:4.3, 1:4.25, 1:4.2, 1:4.1, 1:4, 1:3.9, 1:3.8, 1:3.75, 1:3.7, 1:3.6, 1:3.5, 1:3.4, 1:3.3, 1:3.25, 1:3.2, 1:3.1, 1:3, 1:2.9, 1:2.8, 1:2.75, 1:2.7, 1:2.6, 1:2.5, 1:2.4, 1:2.3, 1:2.25, 1:2.2, 1:2.1, 1:2, 1:1.9, 1:1.8, 1:1.75, 1:1.7, 1:1.6, 1:1.5, 1:1.4, 1:1.3, 1:1.25, 1:1.2, 1:1.1, 1:1, 1.1:1, 1.2:1, 1.25:1, 1.3:1, 1.4:1, 1.5:1, 1.6:1, 1.7:1, 1.75:1, 1.8:1, 1.9:1, 2:1, 2.1:1, 2.2:1, 2.25:1, 2.3:1, 2.4:1, 2.5:1, 2.6:1, 2.7:1, 2.75:1, 2.8:1, 2.9:1, 3:1, 3.1:1, 3.2:1, 3.25:1, 3.3:1, 3.4:1, 3.5:1, 3.6:1, 3.7:1, 3.75:1, 3.8:1, 3.9:1, 4:1, 4.1:1, 4.2:1, 4.25:1, 4.3:1, 4.4:1, 4.5:1, 4.6:1, 4.7:1, 4.75:1, 4.8:1, 4.9:1, 5:1, 5.25:1, 5.5:1, 5.75:1, 6:1, 6.5:1, 7:1, 7.5:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 99:1. In a preferred embodiment the first prodrug to which the range of ratios above relates is aripiprazole cavoxil and the second prodrug is aripiprazole lauroxil. It is also preferable from the point of view of obtaining therapeutic coverage within 24 hours and maintaining it over a period of at least 14 days, for the ratio to be within the range 1:1 to 1:3; or 1:2 to 1:3. In a preferred embodiment the range is 1:3.

Without being bound to theory, it is believed that the selection of the appropriate ratio of each respective prodrug population allows the in vivo release profile to be fine-tuned according to the desired coverage, by virtue of the fact that each respective population's contribution to and effect on the overall release profile of the composition is increased or decreased according to the relative quantity of that particle population in the composition as a whole. Variation of the ratio is therefore a useful tool for tailoring the release profile to attain therapeutic coverage over the desired timepoints.

Release Profiles, Dosage Forms and Administration of the Present Invention

The present invention may be used to provide therapeutic coverage during any lead in period when administering an antipsychotic, preferably aripiprazole based, and most preferably the commercially available product Aristada® (aripiprazole lauroxil extended release injectable suspension; Alkermes Pharma Ireland Limited, Ireland).

Compositions of the present invention, when dosed in vivo, may achieve an aripiprazole concentration above the therapeutically effective amount for aripiprazole within a period of 48 hours and maintain therapeutic coverage for a period of at least 10 days. Preferably, compositions of the present invention, when dosed in vivo, achieve an aripiprazole concentration above the therapeutically effective amount for aripiprazole within a period of 24 hours and maintain therapeutic coverage for a period of at least 10 days, more preferably 14 days and most preferably 21 days. Most preferably, compositions of the present invention, when dosed in vivo, achieve an aripiprazole concentration above the therapeutically effective amount for aripiprazole within a period of 12 hours and maintain therapeutic coverage for a period of at least 10 days, more preferably 14 days and most preferably 21 days.

Compositions of the present invention may be formulated as a dosage form to be administered about once a week. A once-weekly dosage regimen, according to the present invention, can be provided in the form of an intramuscular depot injection, which can be provided as a re-constitutable powder or provided in an injection device, such as a pre-filled syringe.

A once-weekly dosage form may be defined as a dosage that provides a therapeutic concentration in the blood of a human or mammalian subject in less than about 72 hours and which maintains a therapeutic level for a minimum of about 5 days and a maximum of about 13 days. Preferably, a once weekly dosage form reaches a therapeutic concentration in the blood of the subject in less than about 36 hours and maintains a therapeutic level in the blood of the subject for a minimum of about 5 days and a maximum of about 9 days.

The compositions may also be formulated for administration once every two weeks or once every three weeks. In some embodiments, such a composition would reach a therapeutic concentration in the blood of the subject in less than about 7 days, and would maintain a concentration of aripiprazole which is above the therapeutic concentration for a minimum of about 14 days, preferably about 21 days and a maximum of about 28 days. Such a composition could provide an alternative dosing regimen which provides a structure for regular visits to a healthcare professional, but is less stringent and inconvenient for the patient than a once weekly dosing regimen.

The compositions may also be formulated for administration once every two months. In some embodiments, such a composition would reach a therapeutic concentration in the blood of the subject in less than about 7 days, and would maintain a concentration of aripiprazole which is above the therapeutic concentration for a minimum of about 56 days.

Compositions of the present invention may also be formulated as a long acting composition, which can maintain a therapeutic level of active in the blood for at least about 1 week and up to about 1 month. Accordingly, compositions of the present invention can be tailored to a release profile serving as both a lead in and/or a long acting injectable.

The compositions may also be formulated for administration once every two weeks or once every three weeks. In some embodiments, such a composition would reach a therapeutic concentration in the blood of the subject in less than about 7 days, and would maintain a concentration of aripiprazole which is above the therapeutic concentration for a minimum of about 14 days, preferably about 21 days and a maximum of about 28 days. Such a composition could provide an alternative dosing regimen which provides a structure for regular visits to a healthcare professional, but is less stringent and inconvenient for the patient than a once weekly dosing regimen.

Compositions of the present invention, in addition to having a first population of aripiprazole prodrug particles with a volume based particle size (Dv50) of less than about 1000 nm may also include a second population of aripiprazole prodrug particles (different to the first aripiprazole prodrug) which have a larger particle size in the micron range, i.e., having a volume based particle size (Dv50) of about 1000 nm or greater. The first and second particle populations in this context may be referred to as the "nano population" (particle size less than about 1000 nm) and the "micro population" (particle size greater than 1000 nm), respectively. For example, a population of aripiprazole prodrug particles having a volume based particle size (Dv50) of 20 μm can be included in compositions of the present invention as the micro component in order to provide the characteristics of a lead in composition, as described herein, with a long acting release profile in a single composition. In a preferred embodiment, the composition comprises aripiprazole cavoxil as the nanoparticulate component and aripiprazole lauroxil as the microparticulate component.

Therefore, described herein is a simplified dosage regime. In some embodiments, the lead in component provides fast onset and therapeutic levels of aripiprazole in the blood for the duration of the lead in period and the long acting component reaches a therapeutic level in the blood after the lead in period and maintains the therapeutic level over a period of at least about 30 days. This ensures that a single composition maintains therapeutic coverage for a period of at least about 1 to about 30 days. The requirement for separate lead in and long acting injections is therefore avoided, which has the direct consequence of simplifying the dosage regime and improving patient compliance.

It is surprising that a mixed population of particles can be produced as a stable composition at all. The present inventors have observed in relation to mixed populations of other active ingredients that where at least one of the populations has a small (less than about 2000 nm) volume based particle size (Dv50), both populations have a tendency to experience a change in particle size due to the effects of Ostwald ripening. Ostwald ripening is a phenomenon observed in small particle populations where multiple particle sizes are present. Typically, smaller particles dissolve and then re-crystallise, causing the larger particles present to grow. This phenomenon is relatively common with a large number of active agents, particularly active agents having a high solubility. Surprisingly, the incidence of Ostwald ripening in mixed populations of different aripiprazole prodrugs according to the present invention was observed to be very low when measured over a period of 12 weeks.

Compositions of the present invention, in addition to having a first aripiprazole prodrug population of particle size less than about 1000 nm, may include a second aripiprazole prodrug particle population having a volume based particle size (Dv50) which is less than about 1000 nm in size, and at least about 100 nm, at least about 200 nm, at least about 300 nm, at least about 400 nm, at least about 500 nm, at least about 600 nm, at least about 700 nm, at least about 800 nm or at least about 900 nm greater than the Dv50 of the (first) aripiprazole prodrug population.

Compositions of the present invention may be delivered in a dual chamber syringe, in which one of the chambers is provided with a first aripiprazole prodrug composition having a particle size of less than 1000 nm, and a second chamber which is provided with a second aripiprazole prodrug composition having a different particle size than the first composition. For example, the second aripiprazole composition may have a particle size which is also less than 1000 nm, between about 1000 and about 5000 nm or greater than about 5000 nm. Both compositions are thereby stored separately.

In some embodiments, compositions of the present invention are presented in the form of a particulate dispersion. In such a scenario, the composition comprises a dispersion medium in which the population of aripiprazole prodrug particles are dispersed therein.

Such a dispersion may, for example, be provided in an injection device such as a pre-filled syringe. However, it should be understood that an injection device can include any device capable of delivering an injection which may be used with the present invention. For example, the compositions of the present invention may also be administered using an auto-injector device. Alternatively, the compositions of the present invention may be delivered using a needless syringe, or a dual-chamber syringe.

Alternatively, compositions of the present invention may be formulated as a powder for reconstitution in a liquid medium. A significant feature of the present invention in this regard is redispersal of the aripiprazole prodrug particles when reconstituted in a liquid medium. In some embodiments, the redispersed aripiprazole prodrug particles have a volume based particle size (Dv50) of less than about 1000 nm.

One of ordinary skill will appreciate that effective amounts of aripiprazole prodrug can be determined empirically. Actual dosage levels of aripiprazole prodrugs in the composition of the invention may be varied to obtain an amount of each respective aripiprazole prodrug that is effective to obtain a desired therapeutic response for a particular composition and method of administration. The selected dosage level, therefore, depends upon the desired therapeutic effect, the route of administration, the potency of aripiprazole prodrug, the desired duration of treatment, and other factors. Dosage unit compositions may contain amounts of submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

Size Stability of the Present Invention

Aqueous dispersions of microparticulate and nanoparticulate active agents are essentially dynamic systems. To some extent, there is consistently a degree of adsorption and desorption of surface stabilizer which takes place within the composition. The tendency of a particle surface to attract surface stabilizer adsorption thereto is dependent on a number of factors mainly relating to the active agent's physical and chemical properties. These parameters vary greatly between drug substances.

The present invention combines particle populations of at least two distinct aripiprazole prodrugs. In a preferred embodiment the composition comprises a particle population of aripiprazole lauroxil and aripiprazole cavoxil particles. The physical and chemical properties of the aripiprazole prodrugs within the scope of the present invention can vary considerably. For instance, aripiprazole cavoxil was determined to have a solubility in water of less than about 1 µg/ml, whereas aripiprazole lauroxil was determined to have a solubility of less than about 4 ng/mL.

Solubility in water has been found to increase significantly in the presence of polysorbate 20. In a solution comprising 1.5% (w/w) polysorbate 20 at 40° C., at pH 7, the solubility of aripiprazole lauroxil rises to just below about 2 µg/mL, whereas the solubility of aripiprazole cavoxil rises much more significantly to just below about 50 µg/mL. These represent significant differences in the water solubility of the aforementioned prodrugs.

It was a surprising and unexpected discovery that two distinct populations of different aripiprazole prodrug particles according to the present invention could be provided together in a single composition, not least because of the uncertainty that arises as to whether the variation in particle stabilizer affinity for each respective prodrug particle population gives rise to unpredictable size growth in any of the particle populations due to any tendency the stabilizer might have towards one of the particle populations. Furthermore, the differences in solubility might normally present significant challenges to co-formulation of the two particulate populations, because one of the populations may have a tendency to solubilize and recrystallize thereby presenting a route to particle size growth through Oswald Ripening, as described herein. Another potential issue which would discourage against the co-formulation approach of the present invention is the possibility that one of the populations is left with insufficient stabilizer to stabilize the particles due to a higher affinity to the other population. In this scenario, adding additional surface stabilizer may not be an acceptable remedy as this may result in the solubilisation of some particles of the more water soluble population. In any event there is an overall cap on the amount of stabilizer which is acceptable from a patient tolerability standpoint. Nevertheless, it has surprisingly been discovered that in spite of variations in the physical and chemical properties of the prodrugs tested, very stable co-formulations of the aripiprazole prodrugs of the present invention could be produced.

More surprisingly, it has been discovered that a mixed formulation comprising a first component of aripipirazole cavoxil particles of a first given particle size and a second component of aripiprazole lauroxil particles of a second given particle size has improved particle size stability when compared to the same or similar compositions in which the aripiprazole cavoxil and aripiprazole lauroxil populations are provided separately of each other (i.e., by mixing a population of aripiprazole lauroxil particles and a population of aripipriazole cavoxil particles, each respective population having a particle size of less than 1000 nm, the particle size stability for the resultant composition is improved).

Surface Stabilizers

The compositions of the invention comprise at least one surface stabilizer. However, combinations of more than one surface stabilizer have been found to be useful and can be used in the invention. Where a plurality of surface stabilizers is used there may be a primary surface stabilizer that is present in greater concentration than the other (secondary) surface stabilizer(s). For instance, a polyoxyethylene-polyoxypropylene block copolymer having an average molecular weight of about 8,400 (e.g., Pluronic® F68) may be added to improve the rate of release of aripiprazole from the composition. Polyethylene glycol PEG4000 may be added to improve the longer term stability of the composition. It has surprisingly been discovered in the context of the present invention that the addition of secondary stabilizers (such as the aforementioned) may further improve the characteristics of the final composition.

Without being restricted to theory, it is believed that the surface stabilizer functions by forming a steric barrier or an electrostatic barrier around the drug particles, thereby providing enough physical separation of the particles to prevent particle aggregation. Several compounds are known to possess the properties of forming such a steric or electrostatic barrier when applied to small particles. It is therefore plausible that any one of these substances could function as a surface stabilizer in the context of the present invention, and therefore, fall within the scope of the invention. The term surface stabilizer may be used interchangeably with the term surface modifier.

Useful surface stabilizers which can be employed in the invention include, but are not limited to, known organic and inorganic pharmaceutical excipients. Such excipients include various polymers, low molecular weight oligomers, natural products, and surfactants. Exemplary surface stabilizers include non-ionic and ionic (e.g., anionic, cationic, and zwitterionic) surface stabilizers. Without wishing to be bound by any particular theory, it is believed that polymeric materials adhering to a particle surface can present a steric barrier preventing particle aggregation. In the case of ionic surface stabilizers, the stabilizing action may be attributed to electrostatic interactions.

Particularly preferred surface stabilizers for use with the present invention are polysorbate surfactants also referred to as polysorbates or polyoxyethylene sorbitan fatty acid esters. Examples include those available under the Tween® tradename (a registered trademark of Croda Americas LLC limited), such as Tween® 20 (polyoxyethylene 20 sorbitan monolaurate) also referred to as polysorbate 20 or PS20 herein, Tween® 40 (polyoxyethylene 20 sorbitan palmitate), also referred to as polysorbate 40 or PS40 herein, or Tween® 80 (polyoxyethylene 20 sorbitan monooleate), also referred to as polysorbate 80 or PS80 herein. Polysorbates are amphiphilic, nonionic surfactants composed of a hydrophilic head group (sorbitan polyoxyethylene) linked by an ester bond to a hydrophobic tail group. The various grades differ in the length of this tail group, for example PS20 (laurate, C12), PS40 (palmitate, C16), PS80 (oleate, C18).

Other preferred surface stabilizers for use with the present invention include low molecular weight povidones, lecithin. DSPG (1,2-Distearoyl-sn-glycero-3-phospho-rac-(1-glycerol)), DOSS (dioctyl sodium sulfosuccinate, or docusate sodium), methyl and propyl parabens, sorbitan monolaurate, also referred to as SML (available under the trade name Span® 20, a registered trademark of Croda International PLC), carboxymethyl cellulose, hydroxypropylcellulose, also referred to as HPC and including examples such as HPC-SL a low viscosity grade which has a viscosity of 2.0 to 2.9 mPa·s in aqueous 2% w/v solution at 20° C. (available from Nippon Soda Co Ltd, Japan), sodium deoxycholate, and aklsaccharides. Also preferred are block copolymers based on ethylene oxide and propylene oxide, also known as poloxamers and sold for example under the trade names Pluronict and Lutrol® (registered trademarks of the BASF Corporation), and Synperonic (a registered trademark of Croda International PLC). Examples include poloxamer 407 (Lutrol® F127), poloxamer 188 (Lutrol® F68/Pluronic® F68) or Poloxamer 338 (Lutrol® F108/Pluronic® F108). Polaxamers are amphiphilic, nonionic tri-block copolymers consisting of a central hydrophobic poly(propylene oxide) (PPO) block with terminal hydrophilic poly(ethylene oxide) (PEO) blocks. The various grades differ in the length of these blocks and proportion of the hydrophilic content. Poloxamer 188 is (18×100≈) 1800 g/mol and an (8×10≈) 80% of the total is polyoxyethylene; ($PEO_{80}$-$PPO_{27}$-$PEO_{80}$). Poloxamer 338 is (33×1000≈) 3300 g/mol and an (8×10≈) 80% of the total is polyoxyethylene; ($PEO_{132}$-$PPO_{50}$-$PEO_{32}$). It is also envisaged to use only the individual components which make up these block co-polymers, for example, in the case of Pluronic® F108, such individual components are Polyoxyethylene and polyoxvpropylene glycol. It is particularly preferred to use the aforementioned individual components given their approval status. Other preferred stabilizers include TPGS (d-alpha tocopheryl polyethylene glycol 1000 succinate), gelatin and albumin, lysozyme and cyclodextrins (for e.g. betahydroxcyclodextrin). Also useful are gel forming polymers such as ReGel (thermosetting biodegradable gel developed by British Technology Group)(ReGel is a registered trademark of Protherics Salt Lake City, Inc.). Particularly preferred surface stabilizers for use with the present invention are those which are approved by any regulatory authority for the preferred route of administration, intramuscular use.

Of the aforementioned surface stabilizers, the following are particularly preferred as they would generally be considered to be more acceptable for intramuscular use: polysorbate surfactants such as Polysorbate 80, Polysorbate 40 and Polysorbate 20, low molecular weight povidones, lecithin. DSPG, and sorbitan monolaurate. Difunctional block co-polymers such as Pluronic® F-68 (Polyoxyethylene-polyoxypropylene block copolymer), Polyethylene glycol (PEG) based stabilizers (in particular, PEG 4000) are also particularly useful stabilizers in the context of the present invention.

Other useful surface stabilizers include copolymers of vinylpyrrolidone and vinyl acetate or copovidone (e.g., Plasdone® S630, which is a random copolymer of vinyl acetate and vinyl pyrrolidone available from ISP Technologies, Inc (USA)); hydroxypropylmethylcellulose (HPMC, such as Pharmacoat® 603 available from Shin-Etsu Chemical Co Ltd, Japan); a polyvinylpyrrolidone (PVP), such as those available from ISP Corp (New Jersey, USA) under the Plasdone® trade name, e.g. Plasdone® C29/32 (which is equivalent to BASF PVP K29/32), Plasdone® C-30, Plasdone® C17 (equivalent to BASF PVP K-17) and Plasdone® C12 (equivalent to povidone K12); deoxycholic acid sodium salt, sodium lauryl sulphate (SLS also known as sodium dodecyl sulphate or SDS), benzalkonium chloride (also known as alkyldimethylbenzylammonium chloride), lecithin, distearyl palmitate glyceryl or a combination thereof. Other preferred surface stabilizers include albumin. lysozyme, gelatin, macrogol 15 hydroxystearate (available for example from BASF AG under the trade name Solutol® 15), tyloxapol, polyethoxylated castor oil (available for example from BASF AG under the trade name Cremophor® EL), PEG-40 Castor oil (Cremophor® RH 40, a registered trademark of the BASF group), (2-Hydroxypropyl)-3-cyclodextrin, Polyethylene glycol tert-octylphenyl ether (Triton X-100™, a trademark of The Dow Chemical Company), Polyethylene glycol (15)-hydroxystearate (Solutol® HS 15, a registered trademark of the BASF group), and sulfobutyl ether β-cyclodextrin.

The surface stabilizers are commercially available and/or can be prepared by techniques known in the art. Most of these surface stabilizers are known pharmaceutical excipients and are described in detail in the *Handbook of Pharmaceutical Excipients*, published jointly by the American Pharmaceutical Association and The Pharmaceutical Society of Great Britain (R. C. Rowe et al (ed.) 5th Edition, The Pharmaceutical Press, 2006), specifically incorporated by reference.

Excipients

Compositions of the present invention may further comprise one or more non-toxic physiologically acceptable carriers, adjuvants, or vehicles, collectively referred to as carriers. The compositions can be formulated for administration via any pharmaceutically acceptable means, including but not limited to, parental injection (e.g. intramuscular, or subcutaneous). In some embodiments, the small size of the aripiprazole prodrug particles (i.e. less than 1000 nm) makes the composition of the invention particularly advantageous for parenteral formulations.

The compositions of the invention may include a chelating agent such as sodium citrate, EDTA (Ethylenediaminetetraacetic acid), ascorbic acid, Butylated Hydroxyanisole (BHA), potassium metabisulfite, monothioglycerol and L-cysteine. Chelating agents bind with metal ion impurities introduced during the milling process thus preventing the formation of aldehydes.

The present composition may also include a buffer in order to raise and/or stabilize the pH of the dispersion medium. Certain surface stabilizers (in particular, Polysorbate 20) may be susceptible to oxidation. If the polysorbate 20 in a composition oxidises, this may have the effect of lowering the overall pH of the dispersion medium. The drug thereafter may become more soluble in a medium of lower pH, possibly leading to growth in particle size due to processes such as Oswald ripening occurring. A buffer may therefore be included to counter any drop in pH and prevent this effect from occurring. Buffers which may be useful in compositions of the present invention include sodium citrate, sodium phosphate monobasic dihydrate ($NaH_2PO_4$ $2H_2O$), and sodium phosphate dibasic anhydrous ($NaH_2PO_4$).

The present compositions may also include an antioxidant to prevent the oxidation of the surface stabilizer or any other constituent. Citric acid may be used an effective antioxidant.

The compositions of the invention may also comprise a tonicity agent such as saline, sugars or polyols.

As described above, the compositions of the present invention may be formulated as a dispersion, in which case the particles of the present invention are dispersed within a dispersion medium. The dispersion medium may be comprised of water and/or any of the excipients described above. Oils or other non-aqueous media may be used where compatible with the aripiprazole prodrug. Preferably, the dispersion medium is water or an aqueous based medium.

Alternatively, the compositions of the present invention may be presented as particles in a dry form to be dispersed in a dispersion medium prior to administration. In such embodiments, the composition preferably comprises one or more of the above mentioned excipients and is reconstituted in water prior to administration.

Methods of Preparing the Riapiprazole Prodrug Composition of the Invention

The present invention further relates to a method of preparing an aripiprazole prodrug composition according to the present invention.

The method comprises the following steps which may or may not be carried out in sequential order: (a) calculating a quantity of at least one surface stabilizer to be added to the composition, and (b) producing a first population of aripiprazole prodrug particles, most preferably aripiprazole lauroxil or cavoxil, having a volume based particle size (Dv50) of less than about 1000 nm as determined by light scattering. This may be performed using any of the methods described below for producing small particles. The preferred method is milling.

Step (c) involves producing a second population of a second aripiprazole prodrug, different to the first aripiprazole prodrug, which is most preferably aripiprazole lauroxil or cavoxil and which has a Dv50 of greater than, equal to, or less than about 1000 nm.

Step (d) involves combining a quantity of a first surface stabilizer or stabilizer group, most preferably polysorbate 20, with the first population of aripiprazole prodrug particles and a second surface stabilizer or stabilizer group, most preferably also polysorbate 20, with the second population of aripiprazole prodrug particles. Adsorption of surface stabilizer to the respective particles of each population of aripiprazole prodrug may be attained by contacting the particles with surface stabilizer(s) for a time and under conditions sufficient to provide a composition comprising a first particle population, particles of aripiprazole prodrug having a volume based particle size (Dv50) of less than about 1000 nm and a second particle population having a volume based particle size (Dv50) of greater than, equal to, or less than about 1000 nm.

Steps (b), (c) and (d) may be performed simultaneously by milling the respective first and second aripiprazole prodrugs with the stabilizer(s) present, which is described in detail below and in the examples. The first and second aripiprazole prodrugs may be milled together with or without the presence of a surface stabilizer (hereinafter referred to as the "co-milling" approach), or they may be milled separately and mixed together as a separate step post milling (hereinafter referred to as the "co-mixing" approach). Co-milling provides the additional benefit of reducing the number of process steps and is preferential from a process simplification standpoint.

The method may further comprise the step of (e) combining the first and second aripiprazole prodrug particle populations and the surface stabilizer with a dispersion medium to form a dispersed aripiprazole prodrug composition. Further possible steps include (f) combining the first and second aripiprazole prodrug particles with an additional population of aripiprazole prodrug particles having a volume based particle size (Dv50) at least about 100 nm greater in size. The method may optionally include the step of (g) filling the dispersed aripiprazole prodrug composition into an injection device (for example prefilled syringe, autoinjector, needleless syringe or dual chambered syringe. If a dual chambered syringe is used, this can be achieved by filling the aripiprazole prodrug composition into one chamber of the dual chambered syringe, and filling the other chamber of the dual chamber syringe with a second composition. The second composition may be a second aripiprazole prodrug composition, having a different volume based particle size (Dv50) or could be a different aripiprazole prodrug or a non-aripiprazole active ingredient, for example an atypical antipsychotic.

Compositions of the present invention can be made using, for example, milling or attrition (including but not limited to wet milling), homogenization, precipitation, freezing, template emulsion techniques, supercritical fluid techniques, nano-electrospray techniques, or any combination thereof. Exemplary methods of making nanoparticulate compositions are described in U.S. Pat. No. 5,145,684 for "Surface Modified Drug Particles." Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference herein.

Milling to Obtain an Aripiprazole Prodrug Composition

Milling the first and second aripiprazole prodrugs to obtain an aripiprazole prodrug composition according to the present invention comprises dispersing the particles in a liquid dispersion medium in which each respective aripiprazole prodrug is poorly soluble, followed by applying mechanical means in the presence of grinding media to reduce the particle size of the first and second aripiprazole prodrugs to the desired volume based particle size (Dv50). The dispersion medium can be, for example, water, safflower oil, ethanol, t-butanol, glycerine, polyethylene glycol (PEG), hexane, or glycol. A preferred dispersion medium is water.

The first and second aripiprazole prodrugs can be reduced in size (separately or together) in the presence of at least one surface stabilizer. Alternatively, each respective aripiprazole prodrug particle population can be separately, or together, contacted with one or more surface stabilizers as a separate step after attrition. Size reduction can be performed with both aripiprazole prodrugs mixed together and milled at the same time according to the co-milling approach described earlier, or milling of the aripiprazole prodrugs can be performed separately, consistent with the co-mixing approach. Other compounds, such as a diluent, can be added to the first and second aripiprazole prodrug/surface stabilizer composition during the size reduction process. Dispersions can be manufactured continuously or in a batch mode.

The grinding media can comprise particles that are preferably substantially spherical in shape, e.g., ceramic beads or beads consisting essentially of polymeric or copolymeric resin. Alternatively, the grinding media can comprise a core having a coating of a polymeric or copolymeric resin adhered thereon.

In general, suitable polymeric or copolymeric resins are chemically and physically inert, substantially free of metals, solvent, and monomers, and of sufficient hardness and friability to enable them to avoid being chipped or crushed during grinding. Suitable polymeric or copolymeric resins include crosslinked polystyrenes, such as polystyrene crosslinked with divinylbenzene; styrene copolymers; polycarbonates; polyacetals, such as Delrin™ (E.I. du Pont de Nemours and Co.); vinyl chloride polymers and copolymers; polyurethanes; polyamides; poly(tetrafluoroethylenes), e.g., Teflon® (E.I. du Pont de Nemours and Co.), and other fluoropolymers; high density polyethylenes; polypropylenes; cellulose ethers and esters such as cellulose acetate; polyhydroxymethacrylate; polyhydroxyethyl acrylate; and silicone-containing polymers such as polysiloxanes and the like. The polymer can be biodegradable. Exemplary biodegradable polymers or copolymers include poly(lactides), poly(glycolide) copolymers of lactides and glycolide, polyanhydrides, poly(hydroxyethyl methacrylate), poly(imino carbonates), poly(N-acylhydroxyproline)esters, poly(N-palmitoyl hydroxyproline) esters, ethylene-vinyl acetate copolymers, poly(orthoesters), poly(caprolactones), and poly(phosphazenes). For biodegradable polymers or copolymers, contamination from the media itself advantageously can metabolize in vivo into biologically acceptable products that can be eliminated from the body.

The grinding media preferably ranges in size from about 0.01 to about 3 mm. For fine grinding, the grinding media is preferably from about 0.02 to about 2 mm, and more preferably from about 0.03 to about 1 mm in size. The polymeric or copolymeric resin can have a density from about 0.8 to about 3.0 g/cm$^3$.

In a preferred grinding process, the first and second populations of aripiprazole prodrug particles are made continuously. Such a method comprises continuously introducing an aripiprazole prodrug composition according to the invention into a milling chamber, contacting the composition with grinding media while in the chamber to reduce the aripiprazole prodrug particle size, and continuously removing the aripiprazole prodrug composition from the milling chamber. The grinding media is separated from the milled aripiprazole prodrug composition using known separation techniques, in a secondary process such as by simple filtration, sieving through a mesh filter or screen, and the like. Other separation techniques such as centrifugation may also be employed.

An exemplary milling process using a Nanomill® 01 milling system (Alkermes Pharma Ireland Limited) includes the following steps:

1. Calculation of the quantity of active pharmaceutical ingredient (API), surface stabilizer and any other excipient needed for the composition.
2. Preparation of the continuous phase or dispersion medium, which includes the steps of weighing the excipients in a clean vial and vortexing the contents for a number of seconds, allowing the contents to sit for a short period of time thereafter. For preparation of the 10× vehicle, for example, sodium chloride may be dissolved in a citrate buffer. After filtration, the vehicle may be then transferred into a sterile container and stored in cold room.
3. Weighing the API and transferring the API into a milling chamber.
4. Adding the dispersion medium to the API in the chamber.
5. Mixing the content to ensure the surfaces are wetted.
6. Weighing milling media and adding the media to the milling chamber.
7. Mixing the contents of the chamber to ensure most of the media is wetted.
8. Installing the chamber onto the NanoMill® and connecting the cooling bath.
9. Running the mill at its lowest setting for 5 minutes.
10. Milling the content at the desired tip speed and time.
11. Harvesting the milled composition. Where a Nanomill® 01 mill is used, it has been noted that compositions with mean particle size of less than 200 nm are best harvested by centrifuging using a 10 μm harvesting tube or a 10 mL stainless steel harvesting vessel with stainless steel screen having a mesh size ranging from 100 to 150 μm. For compositions having mean particle size of less than 250 nm, it is best to collect most of the NCD using a 23 G needle first and then centrifuge the slurry left using the 10 μm harvesting tube and to combine the two portions thereafter.

An exemplary formulation using polysorbate 20 as a surface stabilizer may be prepared by milling crystals of aripiprazole cavoxil and aripiprazole lauroxil using a Nano-Mill® 01 mill at 30% (w/w) load in 2% (w/w) polysorbate 20. Dosing concentration may be achieved thereafter by diluting the resulting dispersion with vehicle. The potency can be accurately determined by HPLC.

Wet-milling can be conducted in aqueous vehicles containing stabilizing surface modifiers with polystyrene beads (Polymill® 500 polystyrene milling media; Alkermes Pharma Ireland Limited, Ireland) using a NanoMill® 0.01 milling system. The milling shaft tip speed, the milling volume and the milling time may be adapted according to various experimental set-ups until the desired particle size is reached. "Stock" formulations can be harvested by pumping the dispersion through an appropriate filter (10 μm polystyrene or 100 um metal mesh) at approximately 30% (w/w) API load. The solid load, surface stabilizer concentration, milling temperature, the milling shaft tip speed, the milling volume and the milling time may be adapted according to various experimental set-ups until the desired particle size is reached.

Particle Size Characterization

The particle size of the present composition may be measured using techniques such as light scattering, with either water or a dilute surface stabilizer solution as the diluent. Measurements may be verified using microscopy. Particle size distributions may be determined using a Horiba 950 (Horiba Instruments, Inc.; California, USA) particle size analyser as a wet suspension. The volume based particle size (Dv50) is expressed herein by the mean volume diameter of the particles. Particle size measurement can also be carried out using PCS (Dynamic light scattering measurements).

In addition to light scattering techniques, there are other methods for determining particle size as documented below.

Optical microscopy may be conducted on a Leica DMR microscope (Leica Microsystems; Wetzlar, Germany) at 100× magnifications using Phase contrast optics. Image analysis may be performed using Axiovision software.

Scanning electron microscopy (SEM) may be conducted using a suitable scanning electron microscope such as a Phenom Pro G2 (Phenom-World BV; Eindhoven, The Netherlands). Samples may be prepared by casting diluted formulation at about 0.5 mg/mL on to 9 mm Pelcon carbon adhesive tabs, followed by air drying overnight. The samples may be sputter coated (2×) using a Denton Vacuum Desk V sputter coater.

Method of Treatment and Use of the Composition of the Invention

The invention also provides a method of treating a mammal in need comprising administering a stable composition comprising: (a) a first population of particles of a first aripiprazole prodrug, the first population having at least one surface stabilizer adsorbed on the surface of the first aripiprazole prodrug particles, (b) a second population of particles of a second aripiprazole prodrug, the second population having at least one surface stabilizer, which is the same or different to that described in (a) above, adsorbed on the surface of the second aripiprazole prodrug particles, wherein the first and second aripiprazole prodrug both have the formula described by the general formula "Formula 1" disclosed herein, wherein n is zero or an integer from 1 to 20, and the first aripiprazole prodrug has a different value for n to that of the second aripiprazole prodrug and wherein at least one of the first and/or second population of particles has a volume based particle size (Dv50) of less than about 1000 nm.

The compositions of the invention may be useful in the treatment of diseases and disorders of the CNS, such as mental diseases and disorders, including but not limited to schizophrenia, acute manic and mixed episodes associated with bipolar disorder, and other schizophreniform illnesses, major depressive disorder (MDD), and treatment of irritability associated with autistic disorder. The method may include treating a mammal, including a human, for disorders of the central nervous system, such as mental diseases or disorders; such treatments may further include psychiatric treatment in addition to administering to the mammal a composition as described above according to the present invention.

The compositions of the invention can be administered to a subject via any pharmaceutically acceptable means including, but not limited to parenteral administration (e.g., intramuscular, or subcutaneous administration).

A composition suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles including water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The compositions may be administered in any pharmaceutically acceptable form; however, an injectable formulation is preferred.

For example, the injectable formulation may be administered as an intramuscular or subcutaneous injection so as to form a bolus or depot. The depot may allow for a prolonged duration of action, for example, by dissolving slowly and steadily into the subject's system. Thus, the injectable formulations may be configured to allow for the controlled release of the aripiprazole prodrug after, e.g., subcutaneous, intramuscular, or intraperitoneal injection. For example, particle size and excipient concentration may be adjusted to result in the controlled release (e.g., the blood levels of aripiprazole prodrug in the subject's remain within an effective therapeutic window) for greater than about 24 hours, greater than about 3 days, for greater than about 5 days, for greater than about 7 days, for greater than about 10 days, for greater than about 14 days, for greater than about 20 days, for greater than about 30 days, for greater than about 2 months, for greater than about 3 months or for greater than about 4 months, or for any time period in between these values. The compositions may be formulated such that the injected depot may release aripiprazole prodrug at therapeutic levels for periods of from about 24 hours to about twenty-four weeks; from about twenty four hours to about six weeks; from about twenty four hours to about four weeks, from about twenty four hours to about two months, about two to about twenty-four weeks; from about two to about six weeks; from about two to about four weeks; or from about one to about four weeks.

In the treatment of central nervous system disorders, it is useful to provide a drug dosage form that delivers the required therapeutic amount of the drug in vivo and renders the drug bioavailable in a rapid and consistent manner. These goals may be achieved using the injectable formulations of the aripiprazole prodrug composition described herein, via the formation of a depot (e.g., with intramuscular injection) as described above. In some embodiments, the drug is released from the depot into the blood stream at a constant rate, thus providing the patient with the proper dose of the drug continuously for an extended period of time. This method (e.g., depot injection) also results in improved patient compliance. A single injection once per month, for example, will provide the patient with the appropriate therapeutic dosage for the month, versus the daily struggle to remember or to decide to take a tablet, capsule, etc.

An exemplary injectable formulation of the present invention for intramuscular or subcutaneous administration may include a first and second population of aripiprazole prodrug particles wherein at least one of the first and/or second population have a volume based particle size (Dv50) of less than 1000 nm, said first and second particle populations having one or more surface stabilizers, such as but not limited to a polyoxyethylene sorbitan fatty acid ester (polysorbate 80, polysorbate 40, polysorbate 20), low molecular weight povidones, lecithin, d-alpha tocopheryl polyethylene glycol 1000 succinate, dioctyl sodium sulfosuccinate, or docusate sodium, methyl and propyl parabens, sorbitan monolaurate, carboxymethyl cellulose, hydroxypropylcellulose, sodium deoxycholate, akylsaccharides, difunctional block copolymers, d-alpha tocopheryl polyethylene glycol 1000 succinate, gelatin, albumin, lysozyme, cyclodextrins (for example betahydroxcyclodextrin) and gel forming polymers, adsorbed on the surface thereof in an amount sufficient to maintain a volume based particle size (Dv50) for the desired duration of efficacy. Such a composition formulated for parenteral administration may increase efficacy over other aripiprazole or aripiprazole prodrug compositions in the treatment of various types of CNS diseases or disorders, such as mental diseases and disorders.

A composition suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles including water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The compositions of the present invention may also comprise adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

In addition, it is anticipated that a higher concentration of the form of aripiprazole prodrug may be delivered in a smaller injectable dose size (and thus smaller volume) as compared to other compositions of aripiprazole or aripiprazole prodrug. This ensures that any discomfort to the patient when administering is kept to a minimum.

All publicly available documents referenced herein, including but not limited to U.S. patents, are specifically incorporated by reference herein.

EXAMPLES

The following examples are provided to illustrate the present invention. It should be understood, however, that the invention is not to be limited to the specific conditions or details described in these examples.

All units specified in terms of percentages (%) refer herein to percentage weight by weight (% w/w), i.e., the weight of the constituent is expressed as a percentage of the overall weight of the sample prepared.

Horiba: refers to a Horiba LA 910 or LA 950 particle size analyser (Horiba Instruments, Irvine, Calif., USA).

For all of the below examples, milling was performed on a NanoMill® 0.01 milling system (Alkermes Pharma Ireland Limited) which has a chamber size of 10 ml, 50 ml, or 100 ml along with a 500 µm or 250 µm Polymill® polystyrene grinding media (Alkermes Pharma Ireland Limited).

Unless otherwise indicated, materials were sourced as follows: Polysorbate 20. Sodium Citrate and Sodium chloride were supplied by Avantor™ Performance Materials supplied under its J.T.Baker® brand. Avantor Performance Materials, Inc, Philadelphia, USA. Phosphate buffered saline was supplied by either EMD Millipore in the case of sodium phosphate monobasic dihydrate ($NaH_2PO_4$ $2H_2O$) or Avantor™ Performance Materials, J.T.Baker® brand in the case of Sodium phosphate dibasic anhydrous ($NaH_2PO_4$). Arginine-HCL was supplied by Sigma-Aldrich Co. LLC, St. Louis, Mo., USA. Aripirazole lauroxil and aripiprazole cavoxilaripiprazole cavoxil may be produced as described in U.S. Pat. No. 8,431,576. Each of the formulations described below were produced from a solid particulate form. In the case of aripiprazole cavoxil, the particle size (Dv50) prior to milling was greater than 8 microns, and in the case of aripiprazole lauroxil, the particle size (Dv50) prior to milling was greater than 10 microns.

In some cases, abbreviations are used for some components of the composition. For instance, PS20 signifies polysorbate 20, PBS signifies phosphate buffered saline, CBS signifies citrate buffered saline.

Example 1: 200 nm Aripiprazole Cavoxil Formulation (Comparator)

The purpose of this study was to prepare and assess the characteristics of a comparator single aripiprazole prodrug composition of aripiprazole cavoxil having a volume based particle size (Dv50) of approximately 200 nm.

Preparation of Formulation 1 (Comparator)

Formulation 1 was prepared from a crude slurry comprising 26% w/w aripiprazole cavoxil and 1.53% w/w polysorbate 20 as a surface stabilizer (i.e. approximately 17:1 ratio of active to surface stabilizer). To this, 10 mM phosphate buffered saline (pH 6.8) was added along with 26 mM sodium citrate. Polymill milling media of 500 m in size was added, such that the total media load was 80%. The slurry was milled in a NanoMill® 0.01 mill having a 100 ml chamber and pegged shaft at 1000 rpm for 500 minutes at a milling temperature of 15° C. The final composition comprised aripiprazole cavoxil (26% w/w), 1.53% w/w Polysorbate 20, 10 mM phosphate buffer saline and 26 mM sodium citrate. The final composition was determined to have a Dv50 of approximately 200 nm.

Stability Testing of Formulation 1 (Comparator)

Stability testing of Formulation 1 was carried out by taking two samples and maintaining the samples respectively at a temperature of 25° C. and 40° C. over a period of 12 weeks. Particle size measurements were taken at various time points as shown below.

TABLE 1

Stability testing for Formulation 1 (Comparator)

| Time | DV10 (nm) | | DV50 (nm) | | DV90 (nm) | |
|---|---|---|---|---|---|---|
| (Weeks) | 25° C. | 40° C. | 25° C. | 40° C. | 25° C. | 40° C. |
| 0 | 127 | 127 | 202 | 202 | 294 | 294 |
| 1 | 132 | 138 | 213 | 230 | 317 | 348 |
| 2 | 132 | 137 | 213 | 230 | 317 | 348 |
| 4.5 | 136 | 143 | 226 | 245 | 339 | 384 |
| 8 | 134 | 144 | 221 | 247 | 332 | 389 |
| 12 | 136 | 146 | 225 | 254 | 338 | 416 |
| Δ(12-0) | 9 | 19 | 23 | 52 | 114 | 122 |

Δ(12-0) in the table above represents the overall change in particle size which occurred over the 12 week testing period. A plot of the DV50 size measurements for the sample tested at 25° C. is shown in FIG. 1. The Δ(12-0) value at 40° C. is compared against the Δ(12-0) values obtained for Formulations 2, 3, 5 and 6 at 40° C. in FIG. 6.

In Vivo Study of Formulation 1 (Comparator)

A study was performed in rats to assess the in vivo release profile for Formulation 1 (comparator). Blood was assessed over a period of 21 days at various time points to determine the concentration of aripiprazole. The mean concentrations as measured are shown in the table below and are depicted graphically in FIG. 2.

TABLE 2

Mean concentrations of aripiprazole measured In Vivo for Formulation 1 (Comparator)

| Time (Day) | Formulation 1 (Comparator) Aripiprazole concentration (ng/mL) |
|---|---|
| 0.04 | 11.62 |
| 0.21 | 75.60 |
| 0.29 | 106.58 |
| 1 | 95.43 |
| 2 | 42.45 |
| 4 | 18.15 |
| 6 | 47.05 |
| 8 | 64.35 |
| 10 | 43.00 |
| 14 | 14.40 |
| 20 | 2.59 |

Example 2: 200 nm Aripiprazole Lauroxil Formulation (Comparator)

The purpose of this study was to assess the characteristics of a of a comparator single aripiprazole prodrug composition of aripiprazole lauroxil having an volume based particle size (Dv50) of approximately 200 nm.

Preparation of Formulation 2 (Comparator)

Formulation 2 was prepared from a crude slurry (total 136 g) comprising 26% w/w aripiprazole lauroxil and 1.53% w/w polysorbate 20 as a surface stabilizer (i.e. approximately 17:1 ratio of active to surface stabilizer). To this, 10 mM phosphate buffered saline (pH 6.8) was added along with 26 mM sodium citrate. Polymill milling media of 500 μm in size was added, such that the total media load was 80%. The slurry was milled in a NanoMill® 0.01 mill having a 100 ml chamber and pegged shaft at 1000 rpm for 723 minutes at a milling temperature of 5° C. The final composition comprised aripiprazole lauroxil (26% w/w), 1.53% w/w Polysorbate 20, 10 mM phosphate buffer saline and 26 mM sodium citrate. The final composition was determined to have a Dv50 of approximately 200 nm.

Stability Testing of Formulation 2 (Comparator)

Stability testing of Formulation 2 (Comparator) was carried out by taking two samples and maintaining the samples respectively at a temperature of 25° C. and 40° C. over a period of 12 weeks. Particle size measurements were taken at various time points as shown below.

TABLE 3

Stability testing for Formulation 2 (Comparator)

| Time | DV10 | | DV50 | | DV90 | |
|---|---|---|---|---|---|---|
| (weeks) | 25° C. | 40° C. | 25° C. | 40° C. | 25° C. | 40° C. |
| 0 | 126 | 126 | 211 | 211 | 327 | 377 |
| 4 | 128 | 134 | 217 | 235 | 337 | 388 |
| 8 | 130 | 137 | 220 | 249 | 345 | 458 |
| 12 | 132 | 146 | 226 | 270 | 364 | 549 |
| Δ(12-0) | 6 | 20 | 15 | 59 | 37 | 222 |

A plot of the DV50 size measurements for the sample tested at 25° C. is shown in FIG. 1.

In Vivo (Rat) Study of Formulation 2 (Comparator)

A study was performed in rats to assess the in vivo release profile for Formulation 2 (comparator). Rats were dosed with 0.2 mL of Formulation 2. The concentration of prodrug was assessed to be 279 mg/mL. It was calculated therefore that total dose delivered was 56 mg of aripiprazole lauroxil, delivering in effect 38 mg of aripiprazole. Blood was assessed over a period of 21 days at various time points for the aripiprazole. The mean concentrations of these analytes as measured are shown in the table below.

TABLE 4

Mean concentrations of aripiprazole measured In Vivo Formulation 2 (Comparator)

| Time (Day) | Formulation 2 (Comparator) Aripiprazole concentration (ng/mL) |
|---|---|
| 0.04 | NA |
| 0.21 | 2.55 |
| 0.29 | 2.76 |
| 1 | 8.70 |
| 2 | 6.52 |
| 4 | 10.24 |
| 6 | 22.15 |
| 8 | 34.27 |
| 10 | 34.48 |
| 14 | 18.03 |
| 20 | 7.53 |

A plot of the concentration values for aripiprazole is shown in FIG. 2.

Example 3: 200 nm Aripiprazole Cavoxil/Aripiprazole Lauroxil Formulation (1:3 Ratio)

The purpose of this study was to prepare and assess the characteristics of a combined aripiprazole cavoxil and aripiprazole lauroxil composition according to the present invention, in which the cavoxil and the lauroxil components each have a volume based particle size (Dv50) of approximately 200 nm.

Preparation of Formulation 3

Formulation 3 was prepared by co-mixing Formulations 1 and 2. Formulations 1 and 2 were first prepared in full before the mixing step took place to prepare a composition in accordance with the present invention. Formulation 1 and Formulation 2 were mixed at a ratio of 1:3 (i.e. 25% w/w cavoxil to 75% w/w lauroxil).

Stability Testing of Formulation 3

Stability testing of Formulation 3 was carried out by taking two samples and testing the samples respectively at a temperature of 25° C. and 40° C. over a period of 12 weeks. Particle size measurements were taken at various time points as shown below.

TABLE 5

Stability testing for Formulation 3

| Time (weeks) | DV10 | | DV50 | | DV90 | |
|---|---|---|---|---|---|---|
| | 25° C. | 40° C. | 25° C. | 40° C. | 25° C. | 40° C. |
| 0 | 124 | 124 | 206 | 206 | 316 | 316 |
| 4 | 125 | 127 | 209 | 213 | 321 | 331 |
| 8 | 126 | 129 | 212 | 219 | 328 | 346 |
| 12 | 127 | 125 | 212 | 210 | 329 | 324 |
| Δ(12-0) | 3 | 1 | 6 | 4 | 13 | 8 |

A plot of the DV50 size measurements for the sample tested at 25° C. is shown in FIG. 1. The results above indicate that Formulation 3 experiences minimal particle size growth over the period tested and a very high degree of particle size stability.

In Vivo (Rat) Study of Formulation 3

A study was performed in rats to assess the in vive release profile for Formulation 3. Rats were dosed with 0.2 mL of Formulation 3. The concentration of aripiprazole cavoxil was assessed to be 70 mg/mL assuming a formulation density of 1.06 g/mL. It was calculated therefore that total dose of aripiprazole cavoxil delivered was 14 mg. The concentration of aripiprazole lauroxil was assessed to be 202 mg/mL and it was thus calculated that the total dose of aripiprazole lauroxil delivered was 40 mg. The total dose of aripiprazole delivered by the cavoxil and lauroxil components was found to be 37 mg. Blood was assessed over a period of 21 days at various time points to determine the concentration of aripiprazole. The mean concentrations at the time points at which these assessments were made is shown below:

TABLE 6

Mean concentrations of aripiprazole measured in vivo for Formulation 3

| Time (Day) | Formulation 3 Aripiprazole concentration (ng/mL) |
|---|---|
| 0.04 | 10.71 |
| 0.21 | 68.83 |
| 0.29 | 87.18 |
| 1 | 39.55 |
| 2 | 25.65 |
| 4 | 10.03 |
| 6 | 36.05 |
| 8 | 42.68 |
| 10 | 36.75 |
| 14 | 18.68 |
| 20 | 5.65 |

A plot of the concentration values for aripiprazole is shown in FIG. 2. Formulation 3 was found to deliver aripiprazole concentrations above the therapeutically effective level much faster than Formulation 2, and importantly, maintains an acceptably high aripiprazole concentration over the entire testing period of 21 days. The data suggests that Formulation 3 essentially combines the high concentration of aripiprazole timepoint ranges attainable with a single aripiprazole cavoxil (Formulation 1, Comparator) and aripiprazole lauroxil (Formulation 2, Comparator) resulting in the advantages of faster release in relation to the former (Formulation 1) with longer duration in relation to the latter (Formulation 2).

Example 4: 700 nm Aripiprazole Cavoxil Formulation (Comparator)

The purpose of this study was to assess the characteristics of a comparator single aripiprazole prodrug composition of aripiprazole cavoxil having an volume based particle size (Dv50) of approximately 700 nm, in order to evaluate the effect on release profile of such a population of particles when included in a composition according to the present invention.

Preparation of Formulation 4 (Comparator)

Formulation 4 was prepared from a crude slurry comprising 26% w/w aripiprazole cavoxil and 1.53% w/w polysorbate 20 as a surface stabilizer (i.e. approximately 17:1 ratio of active to surface stabilizer). To this, 10 mM phosphate buffered saline (pH 6.8) was added along with 26 mM sodium citrate. Polymill milling media of 500 µm in size was added, such that the total media load was 80%. The slurry was milled in a NanoMill® 0.01 mill having a 100 ml chamber and pegged shaft at 1000 rpm for 65 minutes at a milling temperature of 15° C. The final composition comprised aripiprazole cavoxil (26% w/w), 1.53% w/w polysorbate 20, 10 mM phosphate buffer saline and 26 mM sodium citrate. Particle size analysis confirmed that the Dv50 for this formulation was approximately 700 nm.

In Vivo (Rat) Study of Formulation 4 (Comparator)

A study was performed in rats to assess the in vivo release profile for Formulation 4 (Comparator). The mean concentrations at the time points at which these assessments were made is shown below:

TABLE 7

Mean concentrations of aripiprazole measured In Vivo for Formulation 4 (Comparator)

| Time (Day) | Formulation 4 (Comparator) Aripiprazole concentration (ng/mL) |
|---|---|
| 0.04 | 2.81 |
| 0.21 | 23.15 |
| 0.29 | 19.70 |
| 1 | 17.90 |
| 2 | 17.43 |
| 4 | 17.95 |
| 6 | 39.95 |
| 8 | 70.25 |
| 10 | 47.35 |
| 14 | 20.43 |
| 20 | 4.49 |

Comparison of the In Vivo Release Profiles Obtained for Formulations 1-4.

The pharmacokinetic (PK)s profile following intra-muscular (IM) administration of Formulation 2 in rat exhibits a Tmax of 10 days. Formulation 1 has the same particle size distribution and the composition has exactly the same constituents as Formulation 2 with the exception that the active ingredient is aripiprazole cavoxil. Referring to FIG. 3, the pharmacokinetic profile for Formulation 2 was characterized by a two-stage release profile, where the release of aripiprazole peaks at two different timepoints with an initial peak in concentration observed on or about Day 1 and a second peak in concentration observed on or about Day 8, with a minimum at or about 4 days. With reference to FIG. 2, it is interesting to note that when the two formulations were mixed (Formulation 3), the pharmacokinetic profile seemed to be additive and showed a two-stage release profile and a minimum concentration at 4 days.

Formulation 4 has an identical composition to Formulation 1 but a larger particle size distribution (Dv50 of about 700 nm). The pharmacokinetic profile for Formulation 4 following intramuscular administration in the rat subjects showed a similar two-stage profile to that of Formulation 3 but with lessening or "blunting" of the maximum concentration value for aripiprazole of the first stage, i.e. the first peak. Furthermore, when the pharmacokinetic profiles for Formulations 3 and 4 are compared (see FIG. 4), the aripiprazole concentration at the 4 day minimum was slightly higher for Formulation 4 compared to Formulation 3.

Accordingly, it is reasonable to conclude from this comparison that the peak value in aripiprazole concentration for the first stage release profile and the aripiprazole concentration at the minimum could be adjusted or tuned by changing the ratio of the respective particle populations of the present invention composition and the particle size of a aripiprazole prodrug population.

A comparison of the AUC, Tmax and Cmax for each of the compositions is presented in the table below.

TABLE 8

Comparison of key pharmacokinetic parameters for Formulations 1-4

| | Formulation 1 (Comparator) cavoxil 200 nm | Formulation 2 (Comparator) lauroxil 200 nm | Formulation 3 lauroxil & cavoxil 200 nm (Co-mixed) | Formulation 4 (Comparator) cavoxil 700 nm |
|---|---|---|---|---|
| AUClast (ng*Day/mL) | 665.9 | 368.17 | 514.58 | 566.35 |
| Tmax (Day) | 0.29 | 10 | 0.29 | 8 |
| Cmax (ng/mL) | 106.58 | 34.48 | 87.18 | 70.25 |

Example 5: 200 nm Aripiprazole Cavoxil/Aripiprazole Lauroxil Formulation (1:1 Ratio)

The purpose of this study was to prepare and assess the characteristics of a combined aripiprazole cavoxil and aripiprazole lauroxil composition according to the present invention, in which the cavoxil and the lauroxil components each have a volume based particle size (Dv50) of approximately 200 nm, and in which the cavoxil and Lauroxil are provided in a ratio of 1:1 (i.e. 50% w/w cavoxil to 50% w/w lauroxil).

Preparation of Formulation 5

Formulation 5 was prepared by co-mixing Formulations 1 and 2 as described. Formulations 1 and 2 were first prepared in full before the mixing step took place to prepare a composition in accordance with the present invention. Formulation 1 and Formulation 2 were mixed at a ratio of 1:1.

Stability Testing of Formulation 5

Stability testing of Formulation 5 was carried out by taking two samples, keeping the samples respectively at a temperature of 25° C. and 40° C. over a period of 12 weeks. Particle size measurements were taken at various time points as shown below.

TABLE 9

Stability testing for Formulation 5

| Time (weeks) | DV10 | | DV50 | | DV90 | |
|---|---|---|---|---|---|---|
| | 25° C. | 40° C. | 25° C. | 40° C. | 25° C. | 40° C. |
| 0 | 119 | 119 | 192 | 192 | 289 | 289 |
| 4 | 124 | 125 | 206 | 209 | 314 | 321 |
| 8 | 125 | 126 | 209 | 211 | 324 | 328 |
| 12 | 123 | 126 | 204 | 210 | 311 | 325 |
| Δ(12-0) | 4 | 7 | 12 | 18 | 22 | 36 |

Example 6: 200 nm Aripiprazole Cavoxil/Aripiprazole Lauroxil Formulation (3:1 Ratio)

The purpose of this study was to prepare and assess the characteristics of a combined aripiprazole cavoxil and aripiprazole lauroxil composition according to the present invention, in which the cavoxil and the lauroxil components each have a volume based particle size (Dv50) of approximately 200 nm, and in which the cavoxil and lauroxil are provided in a ratio of 3:1 (i.e. 75% w/w cavoxil to 25% w/w lauroxil).

Preparation of Formulation 6

Formulation 6 was prepared by co-mixing Formulations 1 and 2. Formulations 1 and 2 were first prepared in full before the mixing step took place to prepare a composition in accordance with the present invention. Formulation 1 and Formulation 2 were mixed at a ratio of 3:1.

Stability Testing of Formulation 6

Stability testing of Formulation 6 was carried out by taking two samples and maintaining at a temperature of 25° C. and 40° C. respectively over a period of 12 weeks. Particle size measurements were taken at various time points as shown below.

TABLE 10

Stability testing for Formulation 6

| Time (weeks) | DV10 | | DV50 | | DV90 | |
|---|---|---|---|---|---|---|
| | 25° C. | 40° C. | 25° C. | 40° C. | 25° C. | 40° C. |
| 0 | 118 | 118 | 190 | 190 | 285 | 285 |
| 4 | 122 | 119 | 200 | 193 | 302 | 290 |
| 8 | 123 | 121 | 202 | 199 | 306 | 300 |
| 12 | 121 | 119 | 198 | 194 | 298 | 292 |
| Δ(12-0) | 3 | 1 | 8 | 4 | 13 | 7 |

Comparison of Stability Data for Formulations 1-3 and 5-6

FIG. 6 is a plot of the Δ(12-0) values, i.e. overall change in the Dv50 values, as measured at 40° C. for Formulations 1-3 and 5-6 over a 12 week measurement period. Formulations 3, 5 and 6 show a clearly reduced growth in the Dv50 values when compared with Formulation 1 (Comparator) and Formulation 2 (Comparator). The reduction depicted in FIG. 6 is supportive of the conclusion that the compositions according to the present invention deliver an improvement in particle size stability when compared with formulations where only a single aripiprazole prodrug is present.

What is claimed is:

1. A composition comprising:
   (a) a first population of particles of a first aripiprazole prodrug, said first population of prodrug particles having at least one surface stabilizer adsorbed on the surface thereof, and
   (b) a second population of particles of a second aripiprazole prodrug, said second population of prodrug particles having at least one surface stabilizer adsorbed on the surface thereof,
   wherein said first and second aripiprazole prodrug each have the formula:

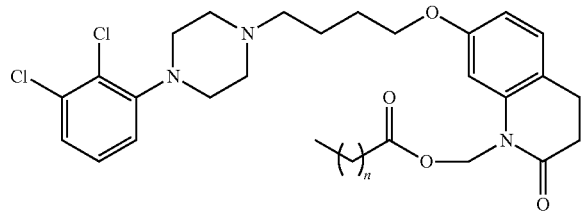

where n is zero or an integer from 1 to 20, and the first aripiprazole prodrug has a different value for n to that of the second aripiprazole prodrug, and
wherein at least one of the first and second populations of particles has a volume based particle size (Dv50) of less than about 1000 nm.

2. The composition of claim 1, wherein the first and second population of particles are provided in a relative amount such that the ratio of the weight of the first prodrug to the weight of the second prodrug is between 1:3 and 3:1.

3. The composition of claim 1, wherein the first and second population of particles are provided in a relative amount such that the ratio of the weight of the first prodrug to the weight of the second prodrug is between 1:1 and 1:4.

4. The composition of claim 1, wherein the n value for the first aripiprazole prodrug is equal to 4.

5. The composition of claim 1, wherein the n value for the second aripiprazole prodrug is equal to 10.

6. The composition of claim 1, wherein the n value for the first aripiprazole prodrug is equal to 4 and the n value for the second aripiprazole prodrug is equal to 10.

7. The composition of claim 1, wherein the volume based particle distribution size (Dv50) of the first and second population of aripiprazole prodrug particles is between about 50 nm and about 700 nm.

8. The composition of claim 1, wherein the volume based particle distribution size (Dv50) of the first population of aripiprazole prodrug particles is between about 175 nm and about 350 nm.

9. The composition of claim 1, wherein the volume based particle size (Dv50) of the first aripiprazole prodrug is between abut 100 and about 300 nm and the volume based particle size of the second aripiprazole prodrug population is between about 200 and about 700 nm.

10. The composition of claim 1, wherein the at least one surface stabilizer is selected from the group consisting of: a polyoxyethylene sorbitan fatty acid ester, low molecular weight povidones, lecithin, d-alpha tocopheryl polyethylene glycol 1000 succinate, dioctyl sodium sulfosuccinate (or docusate sodium), methyl and propyl parabens, sorbitan monolaurate, carboxymethyl cellulose, hydroxypropylcellulose, sodium deoxycholate, akylsaccharides, difunctional block copolymers, gelatin, albumin, lysozyme, cyclodextrins, gel forming polymers, a polyoxyethylene-polyoxypropylene block copolymer and polyethylene glycols.

11. The composition of claim 1, wherein the at least one surface stabilizer is selected from the group consisting of polyoxyethylene sorbitan monolaurate, a polyoxyethylene-polyoxypropylene block copolymer having an average molecular weight of about 8,400 and the polyethylene glycol PEG4000.

12. The composition of claim 1, wherein the ratio of the first and second prodrug to surface stabilizer is within the range from about 0.1:1 to about 40:1.

13. The composition of claim 1, further comprising a dispersion medium in which the first aripiprazole prodrug population of particles and the second aripiprazole prodrug population of particles is dispersed.

14. The composition of claim 1, wherein the composition is provided in an injection device selected from the group consisting of a pre-filled syringe, an auto-injector, a needleless syringe and a dual chambered syringe.

15. A method of treating a condition in a mammal comprising administering to a mammal in need the composition of claim 1, wherein the condition is selected from the group consisting of schizophrenia, bipolar I disorder, major depressive disorder (MDD), autistic disorder, and agitation associated with schizophrenia or bipolar I disorder,
   wherein the composition of claim 1 has a first population of particles of a first aripiprazole prodrug and a second population of particles having a second aripiprazole prodrug, wherein at least one of the populations has a volume based particle size (Dv50) of less than about 1000 nm.

16. A method for preparing a composition according to claim 1, the method comprising the following steps:
   (a) calculating a quantity of at least one stabilizer to be added to the composition,
   (b) producing a first population of aripiprazole prodrug particles having a volume based particle size (Dv50) of less than about 1000 nm,
   (c) producing a second population of a second aripiprazole prodrug, different to the first aripiprazole prodrug, having a volume based particle size (Dv50) of greater or less than about 1000 nm, and
   (d) combining a quantity of at least one surface stabilizer with the first and second populations of aripiprazole prodrug particles, such that the at least one surface stabilizer is adsorbed to the surface of the particles of the first and second particle populations.

17. A composition comprising:
   a mixture of: (i) a population of particles of a first aripiprazole prodrug; and (ii) a population of particles of a second aripiprazole prodrug, wherein the ratio of the first aripiprazole prodrug to the second aripiprazole prodrug is between about 1:99 and 99:1, and wherein at least one of the first and/or second population of particles has a volume based particle size (Dv50) of less than about 1000 nm, and wherein said first and second aripiprazole prodrug have the formula:

wherein n is zero or an integer less than 20.

18. The composition of claim 17, wherein in the first aripiprazole prodrug formula n is equal to 4 and in the second aripiprazole prodrug formula n is equal to 10.

19. The composition of claim 17, wherein the volume based particle distribution size (Dv50) of the first and second population of aripiprazole prodrug particles is between about 50 and about 700 nm.

20. The composition of claim 19, wherein the volume based particle distribution size (Dv50) of the first and second population of aripiprazole prodrug particles is between about 175 nm and about 350 nm.

21. The composition of claim 17, wherein the volume based particle size (Dv50) of the first aripiprazole prodrug is between about 100 and about 300 nm and the Dv50 of the second aripiprazole prodrug population is between about 200 and about 700 nm.

22. The composition of claim 17, wherein said mixture of first and second aripiprazole prodrugs further comprises at least one surface stabilizer.

23. The composition of claim 22, wherein the at least one surface stabilizer is selected from the group consisting of a polyoxyethylene sorbitan fatty acid ester, low molecular weight povidones, lecithin, d-alpha tocopheryl polyethylene glycol 1000 succinate, dioctyl sodium sulfosuccinate (or docusate sodium), methyl and propyl parabens, sorbitan monolaurate, carboxymethyl cellulose, hydroxypropylcellulose, sodium deoxycholate, akylsaccharides, difunctional block copolymers, d-alpha tocopheryl polyethylene glycol 1000 succinate, gelatin, albumin, lysozyme, cyclodextrins and gel forming polymers, a polyoxyethylene-polyoxypropylene block copolymer and polyethylene glycols.

24. The composition of claim 17, wherein the ratio of said mixture of a population of particles of a first and second aripiprazole prodrug composition to surface stabilizer is within the range from about 0.1:1 to about 40:1.

25. The composition of claim 17, further comprising a dispersion medium in which said mixture of a population of particles of a first aripiprazole prodrug and a second aripiprazole prodrug composition is dispersed.

26. The composition of claim 17, adapted for administration as a depot injection.

27. The composition of claim 17, wherein the composition is provided in an injection device.

28. The composition of claim 27, wherein the injection device is a pre-filled syringe.

29. The composition of claim 27, wherein the injection device is an auto-injector.

30. The composition of claim 27, wherein the injection device is a needleless syringe.

31. The composition of claim 27, wherein the injection device is a dual chambered syringe.

32. The composition of claim 31, wherein the first aripiprazole prodrug composition is provided in one chamber of the dual chambered syringe, and the other chamber of the dual chamber syringe is provided with the second aripiprazole prodrug composition.

33. The method of claim 16, whereby the composition when dosed in a mammalian subject reaches a therapeutic level within 24 hours.

34. A method of treating a subject in need with the composition of claim 1, wherein the condition to be treated is selected from the group consisting of schizophrenia, bipolar I disorder, major depressive disorder (MDD), autistic disorder, and agitation associated with schizophrenia or bipolar I disorder, and wherein the treatment comprises:

the administration of a first aripiprazole prodrug having the formula:

and a second aripiprazole prodrug composition having the formula:

wherein the mixture of aripiprazole prodrugs has a volume based particle distribution size (Dv50) of 200 nm, and wherein the ratio of the first aripiprazole prodrug to the second aripiprazole prodrug is 1:3.

35. A composition comprising, consisting of, or consisting essentially of:

a mixture of: (i) a population of particles of a first aripiprazole prodrug; and (ii) a population of particles of a second aripiprazole prodrug, each aripiprazole prodrug having the formula:

wherein n is zero or an integer less than 20, and wherein the volume based particle size (Dv50) of the first aripiprazole prodrug population is between about 100 and about 300 nm and the volume based particle size of the second aripiprazole prodrug population is between about 200 and about 700 nm, and wherein the ratio of the first aripiprazole prodrug to the second aripiprazole prodrug is 1:3.

36. A method of improving initial in vivo pharmacokinetic release profile in a mammal, said method comprising administering a composition comprising, consisting essentially of, or consisting of: a mixture of: (i) a population of particles of a first aripiprazole prodrug having the formula:

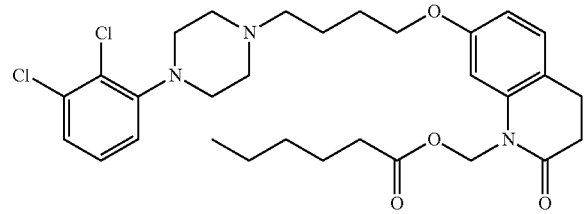 [SMILES: CCCCCC(=O)OCN1C(=O)CCc2ccc(OCCCCN3CCN(c4cccc(Cl)c4Cl)CC3)cc21]

and (ii) a population of particles of a second aripiprazole prodrug having the formula:

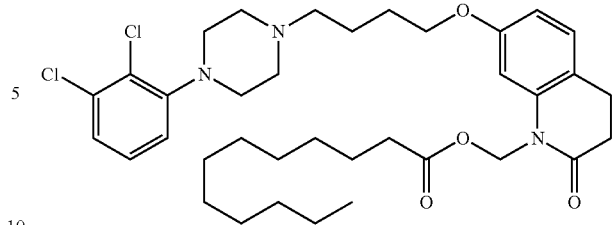

to a mammal, wherein the mixture of aripiprazole prodrugs has a volume based particle distribution size (Dv50) of about 200 nm, wherein the ratio of the first aripiprazole prodrug to the second aripiprazole prodrug is 1:3, and wherein the composition achieves a therapeutic concentration of aripiprazole in the mammal in about 24 hours.

37. The composition of claim 1, wherein the composition further comprises an aqueous carrier.

* * * * *